US008114594B2

(12) United States Patent
Pasloske et al.

(10) Patent No.: US 8,114,594 B2
(45) Date of Patent: Feb. 14, 2012

(54) CRUDE BIOLOGICAL DERIVATIVES COMPETENT FOR NUCLEIC ACID DETECTION

(75) Inventors: Brittan L. Pasloske, Austin, TX (US); Xingwang Fang, Austin, TX (US); Quoc Hoang, Austin, TX (US)

(73) Assignee: Applied Biosysyems, LLC, Carlsbad, CA (US)

( * ) Notice: Subject to any disclaimer, the term of this patent is extended or adjusted under 35 U.S.C. 154(b) by 95 days.

(21) Appl. No.: 12/489,654

(22) Filed: Jun. 23, 2009

(65) Prior Publication Data

US 2010/0167287 A1 Jul. 1, 2010

Related U.S. Application Data

(63) Continuation of application No. 10/866,525, filed on Jun. 11, 2004, now abandoned.

(51) Int. Cl.
*C12Q 1/68* (2006.01)
*C12P 19/34* (2006.01)
*G01N 33/566* (2006.01)

(52) U.S. Cl. ............... 435/6.1; 435/6.12; 435/91.51; 436/501

(58) Field of Classification Search .................. None
See application file for complete search history.

(56) References Cited

U.S. PATENT DOCUMENTS

| | | | |
|---|---|---|---|
| 5,010,183 A | 4/1991 | Macfarlane | 27/536 |
| 5,386,024 A | 1/1995 | Kacian et al. | 536/25.4 |
| 5,399,491 A | 3/1995 | Kacian et al. | 435/91.21 |
| 5,554,516 A | 9/1996 | Kacian et al. | 435/91.21 |
| 5,693,467 A | 12/1997 | Roblin, III et al. | 435/6 |
| 5,817,457 A | 10/1998 | Bird et al. | 435/5 |
| 5,871,975 A | 2/1999 | Kacian et al. | 435/91.2 |
| 5,891,636 A | 4/1999 | Van Gelder et al. | 435/6 |
| 5,932,451 A | 8/1999 | Wang et al. | 435/91.21 |
| 5,973,137 A | 10/1999 | Heath | 536/25.4 |
| 5,990,302 A * | 11/1999 | Kuroita et al. | 536/25.4 |
| 6,143,516 A | 11/2000 | Little et al. | 435/29 |
| 6,316,608 B1 | 11/2001 | Reynolds et al. | 536/22.1 |
| 6,562,575 B1 | 5/2003 | Dahl et al. | 435/6 |
| 6,610,475 B1 | 8/2003 | Kacian et al. | 435/6 |
| 6,664,379 B1 | 12/2003 | Kudlicki et al. | 530/387.9 |
| 6,777,210 B1 | 8/2004 | Pasloske et al. | 435/91.21 |
| 7,163,793 B2 | 1/2007 | Kudlicki et al. | 435/6 |
| 7,264,932 B2 | 9/2007 | Latham et al. | 435/6 |
| 2002/0026046 A1 | 2/2002 | Pasloske et al. | 536/25.4 |
| 2002/0142346 A1 | 10/2002 | Nestor et al. | 435/7.1 |
| 2003/0084471 A1 | 5/2003 | Beach et al. | 800/278 |
| 2003/0104367 A1 | 6/2003 | Rosenow et al. | 435/6 |
| 2003/0104438 A1 | 6/2003 | Eyre et al. | 435/6 |
| 2003/0170617 A1 | 9/2003 | Pasloske | 435/5 |
| 2004/0019196 A1 | 1/2004 | Bair et al. | 536/25.4 |
| 2005/0089857 A1 | 4/2005 | Tada et al. | 435/6 |
| 2005/0118593 A1 | 6/2005 | Potocki et al. | 435/6 |

FOREIGN PATENT DOCUMENTS

| | | |
|---|---|---|
| JP | 09-327291 | 12/1997 |
| WO | WO 91/01384 | 7/1991 |
| WO | WO 94/18156 | 8/1994 |
| WO | WO 94/26867 | 11/1994 |
| WO | WO 99/32654 | 7/1999 |
| WO | WO 02/066637 | 8/2002 |
| WO | WO 03/048386 | 6/2003 |
| WO | WO 03/060116 | 7/2003 |
| WO | WO 2005/042784 | 5/2005 |

OTHER PUBLICATIONS

1988 Stratagene Catalog (cover and p. 39).*
Abelow, B., "Understanding Acid-Base," Lippincott Williams & Wilkins, pp. 30-32, 1988.
Anker et al., "Circulating nucleic acids in plasma or serum," Clinica Chimica Acta, 313:143-146, 2001.
Arts et al., "Cell-type specific DNA-protein interactions at the tissue-type plasminogen activator promoter in human endothelial and HeLa cells in vivo and in vitro," Nucleic Acids Res., 25(2):311-317, 1997.
Brady and Iscove, "Construction of cDNA libraries from single cells," Methods Enzymol., 225:611-623, 1993.
Busche et al., "Expression of angiotensin $AT_1$ and $AT_2$ receptors in adult rat cardiomyocytes after myocardial infarction," J. Am. Pathol., 157(2):605-611, 2000.
Compton, "Nucleic acid sequence-based amplification," Nature, 350, 91-92, 1991.
Dean, J.A., Lange's Handbook of Chemistry (15th Edition). (front matter and pp. 8.30, 8.34 and 8.110; 5 pages total). McGraw-Hill, 1999.
Elbashir et al., "Analysis of gene function in somatic mammalian cells using small interfering RNAs," Methods, 26:199-213, 2002.
Ferre et al., "Preparation of crude cell extract suitable for amplification of RNA by the polymerase chain reaction," Nucleic Acids Research, Oxford University Press, Surrey, GB, p. 2141, 1989.
Fink et al., "Immunostaining for cell picking and real-time mRNA quantitation," Am. J. Pathol., 157(5):1459-1466, 2000.
Fink et al., "Immunostaining and laser-assisted cell picking for mRNA analysis," Laboratory Invest., 80(3):327-333, 2000.
Gaynor et al., "Use of flow cytometry and RT-PCR for detecting gene expression by single cells," Biotechniques, 21: 286-291, 1996.
Godfrey et al., "Quantitative mRNA Expression Analysis from Formalin-Fixed, Paraffin-Embedded Tissues Using 5' Nucleases Quantitative Reverse Trascription-Polymerase Chain Reaction," Journal of Molecular Diagnostics, 2:84-91, 2000.
Klebe et al., "RT-PCT without RNA isolation," BioTechniques, 21(6):1094-1100, 1996.
Li et al., "RNA profiling of cell-free saliva using microarray technology," J Dent Res.; 83(3):199-203, 2004.

(Continued)

Primary Examiner — Samuel Woolwine

(57) ABSTRACT

The invention relates generally to the fields of making biological unit lysates or admixtures of body fluids and of RNA analysis. More specifically, it relates to direct methods for the detection of a specific sequence of RNA in a biological unit, for example a virus, cell or tissue sample, or a body fluid, for example saliva, sputum, blood plasma, etc. More generally, the invention may be used to enzymatically manipulate and protect the RNA in lysate or bodily fluids for a number of applications.

10 Claims, No Drawings

OTHER PUBLICATIONS

Liss, "Improved quantitative real-time RT-PCR for expression profiling of individual cells," *Nucleic Acids Res.*, 30(17):e89-e89, 2002.

Lockhart et al., "Expression monitoring by hybridization to high-density oligonucleotide arrays," *Nat. Biotechnol.*, 14:1675-1680, 1996.

Matsubara et al., "A rapid and sensitive method for HLA-DRB1 typing by acridinium-ester-labeled DNA probes," *Hum. Immunol.*, 35:132-139, 1992.

Mesink et al., "Quantitation of minimal residual disease in Philadelphia chromosome positive chronic myeloid Leukaemia patients using real-time quantitative RT-PCR," *Br. J. Haematol.*, 102:768-774, 1998.

Myers et al., "Reverse transcription and DNA amplification by a Thermus thermophilus DNA polymerase," *Biochemistry*, 30(31):7661-7666, 1991.

O'Leary, "Reducing the impact of endogenous ribonucleases on reverse transcription-PCR assay systems," *Clin. Chem.*, 45(4):449-450, 1999.

Phillips and Eberwine, "Antisense RNA amplification: a linear amplification method for analyzing the mRNA population from single living cells," *Methods*, 10:283-288, 1996.

Retzel et al., "Enzymatic synthesis of deoxyribonucleic acid by the avian retrovirus reverse transcriptase in vitro: optimum conditions required for transcription of large ribonucleic acid templates," *Biochemistry*, 19(3):513-518, 1980.

Silva et al., "Detection of epithelial tumour RNA in the plasma of colon cancer patients is associated with advanced stages and circulating tumour cells," *Gut*, 50(4):530-4, 2002.

Su et al., "High-throughput RT-PCT analysis of multiple transcripts using a microplate RNA isolation procedure," *BioTechniques*, 22:1107-1113, 1997.

Tang et al., "A polymerase chain reaction based method for detecting Mycoplasma/Acholeplasma contaminants in cell culture," *J. Microbiol. Methods*, 39:121-126, 2000.

Tyagi and Kramer, "Molecular beacons: probes that fluoresce upon hybridization," *Nat. Biotechnol.*, 14(3):303-308, 1996.

Ungefroren et al., "Transcriptional Regulation of the Human Biglycan Gene," *Journal of Biological Chemistry*, 271:15787-15795, 1996.

Yan et al., "One-tube protocol for single-cell reverse transcriptase-polymerase chain reaction," *Anal. Biochem.*, 304:267-270, 2002.

International Search Report mailed Oct. 4, 2005 in PCT/US2005/020602 entitled "Crude Biological Derivatives Competent for Nucleic Acid Detection;" Inventors: Pasloske, et al.; Applicant: Ambion, Inc.

USPTO issued Office Action mailed Jul. 26, 2006 in U.S. Appl. No. 10/866,525, filed Jun. 11, 2004 entitled "Crude Biological Derivatives Competent for Nucleic Acid Detection;" Inventors: Pasloske, et al.; Assignee: Applera Corporation.

USPTO issued Office Action mailed Apr. 17, 2007 in U.S. Appl. No. 10/866,525, filed Jun. 11, 2004 entitled "Crude Biological Derivatives Competent for Nucleic Acid Detection;" Inventors: Pasloske, et al.; Assignee: Applera Corporation; (AMBI:100US / 6549US).

USPTO issued Office Action mailed Oct. 30, 2007 in U.S. Appl. No. 10/866,525, filed Jun. 11, 2004 entitled "Crude Biological Derivatives Competent for Nucleic Acid Detection;" Inventors: Pasloske, et al.; Assignee: Applera Corporation.

USPTO issued Office Action mailed Jun. 16, 2008 in U.S. Appl. No. 10/866,525, filed Jun. 11, 2004 entitled "Crude Biological Derivatives Competent for Nucleic Acid Detection;" Inventors: Pasloske, et al.; Assignee: Applera Corporation.

USPTO issued Office Action mailed Jan. 23, 2009 in U.S. Appl. No. 10/866,525, filed Jun. 11, 2004 entitled "Crude Biological Derivatives Competent for Nucleic Acid Detection;" Inventors: Pasloske, et al.; Assignee: Applera Corporation.

Written Opinion of the International Searching Authority mailed Oct. 4, 2005 in PCT/US2005/020602 entitled "Crude Biological Derivatives Competent for Nucleic Acid Detection;" Inventors: Pasloske, et al.; Applicant: Ambion, Inc.

International Preliminary Report on Patentability mailed Dec. 14, 2006 in PCT/US2005/020602 entitled "Crude Biological Derivatives Competent for Nucleic Acid Detection;" Inventors: Pasloske, et al.; Applicant: Ambion, Inc.

* cited by examiner

SEQUENCE LISTING

<160> NUMBER OF SEQ ID NOS: 37

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic Primer

<400> SEQUENCE: 1
gctcaataat cgcctcactt gtg     23

```
<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
caacaaaggg tactcgtcta tactatataa gc                                    32

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
tagccaggcg tttcccgcgt tt                                               22

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
ccagaagtgg aatctttaca ggac                                             24

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
caagtttttg acatgggatg ct                                               22

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
tacatttccc aaatggaaac caggaagc                                         28

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
caccagggct gcttttaact ct                                               22

<210> SEQ ID NO 8
```

```
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
tggaatcata ttggaacatg taaacc                                          26

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
atattgttgc catcaatgac cccttcattg                                      30

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
aggctggact cggattcgt                                                  19

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
tccatcacca acaatcacca gt                                              22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
ctgagcaatg gctgccatcc gg                                              22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
acgttaacag tgggtgccaa                                                 20

<210> SEQ ID NO 14
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      Primer

<400> SEQUENCE: 14
ccccgacggt ctctcttca                                                    19

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
tcatgctaac gcagcagttg caaaca                                            26

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
actccacggc gtctcagga                                                    19

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
gcgcgcgatg aatttgtg                                                     18

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
ccaaccgctt cgcccgcaaa                                                   20

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
gatcgagtac atcttcaagc catc                                              24

<210> SEQ ID NO 20
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      Primer

<400> SEQUENCE: 20
ctcgtcattg cagcagcc                                                   18

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
tgtgtgcccc tgatgcgatg c                                               21

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
ccccaacaat ctgagccca                                                  19

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
gggtcccaga tactggtgcc                                                 20

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
tcacagccga aaacccccgt gc                                              22

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
tcaagaacga aagtcggagg                                                 20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer
```

<400> SEQUENCE: 26
ggacatctaa gggcatcaca                                              20

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
tggctgaacg ccacttgtcc ctctaa                                       26

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
cgcctccctg gacaagttc                                               19

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 29
gctccagctt aacggtattt gg                                           22

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 30
tggcttctgt gagcaccgtg ctg                                          23

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 31
gctggcccat cactttgg                                                18

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 32

```
ccagccacca ctttctgata gg                                              22
```

```
<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 33
agaattcacc ccaccagtgc aggc                                            24
```

```
<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 34
ggcgcagtgc ttctctacag                                                 20
```

```
<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 35
tagggtctcg tcccgcttc                                                  19
```

```
<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 36
ttctccagac ccaccacacc gc                                              22
```

```
<210> SEQ ID NO 37
<211> LENGTH: 1036
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 37
gggagaagac ugcggcauau aagcgcucaa uggcccuuac uuguugccua gauuauauua    60
aagauccaua cguuaccugc caaccgucaa cuccccgacg uccuuuacuu gagaacaucg   120
agcaaaucuu cugccaccua agcggccgca gccuaaagau uacuuaguuc uguugggugc   180
ugcaauaaca acaaagggua cucgucuaua cuauauaagc gcgauaauau cuagaaacgc   240
gggaaacgcc uggcuaguca ucgcacaagu gaggcgauua uugagccaau caucggcgau   300
uaacuuaaag aaaagcgggu acgggauauc gcuaugugcc gcggcaaagg cugccaacau   360
aaaaugugca agcguaaaug cagcguccau gguaaaauua guugagccu ugaugucuua    420
```

-continued

| | | | | | |
|---|---|---|---|---|---|
| gaugauccac | uaaucggcua | cccuugcuag | uagguguaga | uucucgaaaa | gucuuuuagu 480 |
| aggugauccu | cugguacguc | auauaauaua | ucugcucuau | auagccacuu | ccacgcuuag 540 |
| aucuccgugc | ucaucaccau | ccguagaucg | ucgaccucuc | auacucuagu | cacuguggug 600 |
| uucgugggug | cagguauuga | caggcucaua | cauauaauau | gaaauugggc | cuuccgcagc 660 |
| ucugaacuau | cgagcuuccu | ucuaagaaug | aauguuggga | agcccgauuu | gauaaacgca 720 |
| cggcgcaaua | gcuaaacaga | ucuuaggagu | uucaccacug | gagucagcgu | aaauacacug 780 |
| aucuugcgaa | aauaguuggc | ggucuuauaa | acugaguaga | gcgcgcuugc | guccaauacg 840 |
| auuagauucc | aaccgcgaug | ccacuauggc | guacaaauaa | gaauguuuuc | aaggggauaa 900 |
| gauggaguca | ucuggccgcg | uaacccuaca | aaaaaaauga | accguaauag | agcaguugua 960 |
| caucgagacg | uacguugcac | gaaaaauagu | gacuuuacgu | caguacaaaa | aaaaaaaaaa 1020 |
| aaaaaaaaaa | aaaaaa | | | | 1036 |

CRUDE BIOLOGICAL DERIVATIVES COMPETENT FOR NUCLEIC ACID DETECTION

The present application is a continuation application of, and claims priority to, pending U.S. patent application Ser. No. 10/866,525 filed Jun. 11, 2004, to Pasloske et al., which patent application is incorporated by reference herein in its entirety.

The government may own rights in the present invention pursuant to grant number R44 HL69718 from National Institutes of Health/National Heart, Lung, and Blood Institute.

BACKGROUND OF THE INVENTION

1. Field of the Invention

The present invention relates generally to the fields of making biological unit lysates or admixtures of body fluids for RNA analysis. More specifically, it teaches a more direct method for the detection of a specific sequence of RNA in a biological unit, for example a virus, cell or tissue sample, or a body fluid, for example saliva, sputum, blood plasma, etc. More generally, the invention may be used to enzymatically manipulate and protect the RNA in lysate or bodily fluids for a number of applications.

2. Description of Related Art

There are many molecular biology techniques that can be used to analyze RNA or RNA-containing samples. For example, reverse transcription followed by the polymerase chain reaction (RT-PCR) is one of the main methods used for measuring mRNA levels from cells or other biological samples such as viruses. Additionally, reverse transcription is the first step of several different strategies for labeling or amplifying a small quantity of RNA for the purpose of expression profiling (U.S. Pat. No. 5,554,516; U.S. Pat. No. 5,891,636; Phillips, 1996; Lockhart, 1996; U.S. Pat. No. 6,316,608). Those of ordinary skill in the field know many other such RNA-based techniques.

In most cases, prior to performing any enzymatic methods, the substrate RNA is isolated from a biological sample to prevent the degradation of the RNA and to remove inhibitors of the enzymatic processes used to analyze the RNA. Current procedures for RNA isolation involve numerous steps and are not very amenable to high throughput analysis. Some procedures require the use of enzymes, such as proteinase K, pepsin, or DNase or the use of DNA or protein precipitating agents to "clean up" the RNA containing sample prior to use. Some require the use of temperature variation, such as freezing of samples, or heating of reaction mixtures to obtain RNA that is appropriate for use. Further, some of these procedures require the use of RNase inhibitors in their reaction mixtures. Also, many of these procedures have fairly defined limits on the numbers of cells that can be employed in the respective procedures. Currently, the majority of samples are probably processed using high concentrations of chaotropic or denaturing reagents as a first step to disrupt the sample. As such, the RNA must be isolated from these disruptive reagents before it can be processed enzymatically for analysis since the enzymes would be inactive in the presence of these reagents. For these reasons, many prior art techniques are not amenable to easy practice in the laboratory and also not amenable to automation.

A procedure that resolves one or more of the above-referenced problems and enables the direct use of a cell lysate or body fluid sample for RNA-based techniques immediately after the addition of a buffer at room and/or ambient temperature would be highly beneficial and more adaptable to automation.

SUMMARY OF THE INVENTION

The present invention, in general terms, provides for a procedure that enables the direct use of samples containing RNA. In various embodiments, the methods and buffers of the invention resolve one or more of the problems discussed above. For example, the methods and buffers of the invention can result in: rapid preparation of samples; samples containing RNA that is stable for the purpose for which it will be used in preparations of samples without the need for temperature variations, addition of proteins, chaotropic agents, DNA and/or protein precipitating agents, high salt, etc.; samples with high cell concentrations; reaction mixtures comprising a high level of RNA in terms of RNA equivalents; RT-PCR reaction mixtures with Ct values that compare favorably with reaction mixtures produced by more laborious means; RNA containing lysates or admixtures that can be produced and stored at room, ambient, and/or laboratory bench temperature. These samples also contain the entire genomic DNA content of the original sample, which is useful for normalizing samples by using a target in genomic DNA as an internal standard instead of 18S rRNA. The concentration of genomic DNA does not vary. Most other RNA isolation procedures lead to some loss of genomic DNA, and, therefore, genomic DNA could not be used as an internal standard. Of course, it is not necessary that the invention result in all of these advantages in all circumstances, or even in at least one of these advantages in all circumstances. The ability of the invention to result in any one of these advantages in certain circumstances provides value to the invention. Those of skill in the art will, upon reading this specification, be able to implement the invention in appropriate circumstances and realize appropriate advantages.

In broad embodiments, the invention relates to methods comprising: obtaining a sample containing RNA; obtaining a buffer; mixing the sample and the buffer; and forming a lysate or admixture in which the RNA is protected from substantial degradation. In some cases, this protection may be accomplished by precipitation of the RNA in the lysate or admixture through the use of a low pH buffer, a high pH buffer, or a buffer containing an agent that brings about precipitation of the RNA and/or inactivation of ribonuclease in the lysate or admixture. "Precipitation" is defined as separating a majority of the RNA from the lysate or admixture, or rendering the RNA such that it can be separated, for example, via either centrifugation to pellet the RNA or collecting the RNA on a filter. The buffer may be a low pH buffer or a high pH buffer. The buffer may comprise a detergent, for example, but not limited to, a non-ionic detergent, an anionic detergent or a cationic detergent. Additional descriptions of some of the embodiments of the invention follow.

The lysates and admixtures of the sample and the buffer can be used essentially immediately after the addition of a buffer at room temperature or another appropriate temperature. Additionally, the invention provides for buffers that allow for such procedures to be practiced. In some more specific embodiments, the admixtures are employed in RT-PCR procedures.

As described elsewhere in the specification and known to those of skill in the art, the invention may be applied to compositions or samples comprising at least one biological unit containing RNA or samples comprising RNA not comprised in a biological unit.

The term "biological unit" is defined to mean any cell or virus that contains genetic material. In most aspects of the invention, the genetic material of the biological unit will include RNA. In some embodiments, the biological unit is a prokaryotic or eukaryotic cell, for example a bacterial, fungal, plant, protist, animal, invertebrate, vertebrate, mammalian, rodent, mouse, rat, hamster, primate, or human cell. Such cells may be obtained from any source possible, as will be understood by those of skill in the art, for example, a prokaryotic or eukaryotic cell culture. The biological unit may also be obtained from a sample from a subject or the environment. The subject may be an animal, including a human. The biological unit may also be from a tissue sample or body fluid, e.g., saliva, plasma, serum, urine, whole blood, sputum, fecal matter or cerebral spinal fluid. The biological unit may be obtained from a leukocyte enriched blood fraction, which may be produced in any manner known to those of skill in the art, for example, the ammonium chloride method of lysing red blood cells or methods involving selective filtering of leukocytes. Further, the biological unit may be stored in or obtained from a sample stored in an RNA preservation medium, such as the medium sold by Ambion under the RNAlater® name, and described in U.S. patent application Ser. Nos. 09/160,284 and 09/815,577, both of which are entitled "Methods and Reagents for Inactivating Ribonucleases, and the full disclosures of both of which are incorporated herein by reference.

Samples comprising RNA not comprised in a biological unit include, but are not limited to, body fluids and samples comprising fully or partially purified RNA. The term "body fluid" is defined to mean any body fluid that does or may contain RNA. For example, the body fluid may be saliva, sputum, whole blood, plasma, serum, cerebral spinal fluid, fecal matter, or urine. The body fluid may be obtained from an animal, including a human, via any appropriate means as known to those of skill in art. Of course, those of skill will be able to determine any number of RNA containing units or compositions to which the present invention may be applied.

In some embodiments, the invention relates to methods comprising: obtaining at least one biological unit containing RNA or sample comprising RNA not comprised in a biological unit; obtaining a low pH buffer; mixing the biological unit and the buffer to prepare a low pH lysate or mixing the sample and the buffer to prepare a low pH admixture; and mixing at least a portion of the lysate or admixture with a composition comprising enzyme using RNA as a substrate to form a reaction mixture.

The inventors have found that such low pH lysates and admixtures are capable of use in a wide variety of molecular biology techniques, and have the benefit of protecting RNA in the lysate or admixture from degradation for sufficient time to allow for such molecular biology techniques to be performed without concern for RNA degradation. Additionally, lysates and admixtures of the invention can be used at normal ambient or room temperature, without artificial control or modulation of the temperature of the lysate or admixture or a reaction mixture comprising all or part of the lysate or admixture. Of course, this does not mean that molecular biology techniques, such as PCR, which rely upon variations in temperature cannot be employed with lysates according to the invention or reaction mixtures comprising such lysate or admixture. Rather, it means that many of the lysates of the invention do not require temperature variations in order to prevent RNA degradation.

In its broadest sense in the context of the invention, the definition of "low pH" is any pH below 7 that allows for the objects of the invention to be realized. For example, lysate pHs of equal to or below 6.5, equal to or below 6.0, equal to or below 5.5, equal to or below 5.0, equal to or below 4.5, equal to or below 4.0, equal to or below 3.5, equal to or below 3.0, equal to or below 2.5, and equal to or below 2.0, are expected to be of use in some embodiments of the invention. Further, it is contemplated that lysate or admixture pH ranges between any two of the above-described points will be useful in the context of the invention. In preferred embodiments of this aspect of the invention, the low pH buffer is one that, when added to the biological unit or sample comprising RNA not comprised in a biological unit in an appropriate amount results in a low pH biological unit lysate or admixture that has a pH of from 0 to 6. In preferred embodiments, the low pH lysate or admixture has a pH of 1 to 5.5. In currently favored embodiments, the lysate or admixture has a pH of less than 5. In some more preferred embodiments, the pH is between 1.5 and 4.0, with a pH of 2.0 to 3.0 being even more preferred. In some most preferred embodiments, the pH is about 2.5. Of course, those of skill in the art will realize that, for most applications, the low pH buffers of and employed in the practice of the invention may need to be of lower pH than that ultimately desired in the lysate or admixture, because of dilution that can occur when one mixes the biological units or sample comprising RNA not comprised in a biological unit with the buffer.

Once a low pH lysate or admixture of the invention is prepared, the RNA in it is typically stabilized for a relevant period of time at ambient, or another relevant, temperature. The lysate or admixture can then be employed in any of the wide variety of molecular biological techniques such as RT-PCR, the preparation of cDNA, cloning, Nucleic Acid Sequence Based Amplification (NASBA), labeling RNA for use in expression analysis, RNA amplification, microarray analysis, transcription mediated amplification (TMA), etc. In some embodiments, the lysate or admixture, or a portion thereof, will be added to another component in the process of performing a molecular biology technique, to form a reaction mixture. In such cases, it may be necessary to have the pH of the reaction mixture be higher, or in some cases even lower, than the pH of the lysate or admixture. This will be the case in regard to some molecular biology techniques that rely upon enzymes that are active, or at least maximally active in a pH range that is higher than the pH range of the low pH lysate or admixture.

In some preferred embodiments, the method of the invention further comprises adding or mixing at least a portion of the lysate or admixture with a composition comprising reverse transcriptase to form a reverse transcriptase reaction mixture and incubating the reaction mixture under conditions resulting in a reverse transcription reaction. In such embodiments, the reverse transcriptase may be comprised in a reverse transcriptase buffer that raises the pH of the reaction mixture to a level suitable for reverse transcriptase function. Alternatively, a further component or buffer that acts to raise the pH may be added to the lysate or admixture before the addition of the reverse transcriptase or to the reaction mixture. In many reaction mixtures, the final pH of the reaction mixture will be between 7.0 and 9.5, with a pH of between 8.0 and 8.4 being particularly preferred for some reverse transcriptases, and a pH of about 8.3 being especially preferred in some embodiments. Those of skill in the art will understand that a variety of reverse transcriptases, as discussed below and elsewhere in the specification and known to those of skill in the art, can be employed in the context of the invention. The reverse transcriptase buffer may contain any suitable buffer in any suitable concentration, and those of skill will be able to select and formulate such buffers. One embodiment comprises 50 mM TRIS at pH 8.3.

Any reverse transcriptase known to those of skill in the art or discovered after the time of the filing of this application is anticipated to be useful in the context of the invention. MMLV-RT (murine maloney leukemia virus-reverse transcriptase) is one of the most commonly used reverse transcriptases by molecular biologists. However, there are other reverse transcriptases that function in the invention. By way of non-limiting example, Avian Myelogenous Virus reverse transcriptase (AMV-RT; Retzel, 1980), human immunodeficiency virus (HIV)-RT (Muller, 1989) and the Tth DNA polymerase (Myers, 1991), which also has reverse transcriptase activity, can each synthesize cDNA. Further, the Tth DNA polymerase has reverse transcriptase activity if $Mn^{+2}$ is provided in the buffer and can be used to generate cDNA from a lysate or admixture following the protocol of the invention. Those of skill in the art will understand that the above-described nucleic acid polymerases and any other nucleic acid polymerases having reverse transcriptase activity can be adaptable to the protocols of the invention and will be able to select appropriate reverse transcriptases and employ them under appropriate conditions in reaction mixtures by following the teachings of this specification.

The invention, in some cases, provides benefits in that it is not necessary to incubate the lysate or admixture or a portion thereof with a DNase, proteinase K, pepsin or other catabolic enzyme prior to mixing at least a portion of the lysate or admixture with a composition comprising reverse transcriptase or another enzyme. Additionally, there is no need, in most embodiments, for the invention to subject the lysates, admixtures, and/or reaction mixtures of the invention to treatment with DNA and/or protein precipitating agents to achieve reverse transcription or another desired enzymatic action. For many molecular biology procedures, this provides for streamlining of a process. Of course, there is no reason why those of skill in the art could not, in some embodiments, add DNase, proteinase K, pepsin or precipitating agents to the lysate or admixture. However, such additives are not required in many embodiments of the invention. Additionally, in many embodiments RNA need not be not isolated from the lysate or admixture prior to mixing at least a portion of the lysate or admixture with a composition comprising reverse transcriptase or another relevant enzyme.

In some preferred embodiments, at least one cDNA product of a reverse transcription reaction mixture as described above is amplified. This amplification can be done by any manner known to those of skill in the art. In many embodiments, the amplification will be done by the polymerase chain reaction (PCR), in which case the method is a method of "RT-PCR." In some embodiments the reaction will be a two-step real-time PCR procedure, although a wide variety of variations in PCR procedures may be employed. Also, "nested" PCR, as known to those of skill in the art, can allow for great sensitivity in some embodiments. It is also possible that the invention may be used in conjunction with isothermal amplification methods such as transcription mediated amplification (TMA; U.S. Pat. No. 5,399,491) or Nucleic Acid Sequence-Based Amplification (NASBA; Compton, 1991). This amplification system typically is comprised of at least 3 different enzymes (reverse transcriptase, DNA-dependent DNA polymerase and a DNA-dependent RNA polymerase, and in some cases comprises RNase H) that function together to generate multiple copies of an RNA. The levels of the amplified RNA correlate with the pre-amplified concentration of the target sequence. Thus, instead of using RT-PCR, TMA could be used to quantify the levels of an mRNA in a sample. For example, cells from tissue culture or from blood are lysed using the buffer and then the cell lysate or admixture is added to reaction mixture containing all the components to perform TMA or NASBA and amplify the sequence of a specific mRNA or virus. The amplified RNA can then be detected using one of several methods including the hybridization protection assay (HPA; Matsubara, 1992) or molecular beacons (Tyagi, 1996). Those of skill will be able to use these exemplary amplification techniques, and any others known at the time of filing or later developed, in the context of the invention.

A further advantage of the present invention is that, in some embodiments, it allows for the processing of samples with high cell concentrations. This ability to use high cell concentrations can provide advantages in any of the procedures discussed above or known to those of skill in the art. For example, many prior RT-PCR techniques are limited to the use of samples containing less than 1, 1-10, 30, 40, 50, 60, 75, or 100 cells/μl of buffer. When a sample is added to a reverse transcriptase reaction, the concentration of cellular equivalents of RNA components in the reaction mixture is even less. For example, Gaynor et al. (1996) teach that one can use the 1 to 1000 cells in a 20 μl RT reaction, i.e., 0.05 to 50 cells per μl of reaction. Given standard dilutions that occur in making cell sample lysates or other RNA containing admixtures into reverse transcriptase reaction, most prior techniques begin with reaction mixtures comprising the RNA of less than one to about 50 cells. The buffers and techniques of the present invention certainly work in the context of low cell concentrations. However, they also allow for higher concentrations of cells to be used. For example, using the methods and buffers of the invention, it is possible to make cellular lysates of 5000 cells per μl, 2000 cells per μl, 1500 cells per μl, 1000 cells per μl, 900 cells per μl, 800 cells per μl, 750 cells per μl, 700 cells per μl, 650 cells per μl, 600 cells per μl, 550 cells per μl, 500 cells per μl, 450 cells per μl, 400 cells per μl, 350 cells per μl, 300 cells per μl, 250 cells per μl, 200 cells per μl, 175 cells per μl, 150 cells per μl, 125 cells per μl, 100 cells per μl, 90 cells per μl, 80 cells per μl, 75 cells per μl, 70 cells per μl, 65 cells per μl, 61 cells per μl, 55 cells per μl, 51 cells per μl, 50 cells per μl, 45 cells per μl, 41 cells per μl, 40 cells per μl, 35 cells per μl, 31 cells per μl, 30 cells per μl, 25 cells per μl, 21 cells per μl, 20 cells per μl, 18 cells per μl, 16 cells per μl, 15 cells per μl, 14 cells per μl, 12 cells per μl, 11 cells per μl, 10 cells per μl, 9 cells per μl, 8 cells per μl, 7 cells per μl, 6 cells per μl, 5 cells per μl, 4 cells per μl, 3 cells per μl, 2 cells per μl, 1 cell per μl, 0.9 cell per μl, 0.8 cell per μl, 0.7 cell per μl, 0.6 cell per μl, 0.5 cell per μl, 0.4 cell per μl, 0.3 cell per μl, 0.25 cell per μl, 0.20 cell per μl, 0.15 cell per μl, 0.1 cell per μl, 0.05 cell per μl, and/or of any concentration range defined by any of these points, or any lower cell concentration. Further, it is possible, according to the invention to make RT-PCR reaction mixtures comprising concentrations of cellular RNA equivalent to 1500 cells per μl, 1000 cells per μl, 900 cells per μl, 800 cells per μl, 750 cells per μl, 700 cells per μl, 650 cells per μl, 600 cells per μl, 550 cells per μl, 500 cells per μl, 450 cells per μl, 400 cells per μl, 350 cells per μl, 300 cells per μl, 250 cells per μl, 200 cells per μl, 175 cells per μl, 150 cells per μl, 125 cells per μl, 100 cells per μl, 90 cells per μl, 80 cells per μl, 75 cells per μl, 70 cells per μl, 65 cells per μl, 61 cells per μl, 55 cells per μl, 51 cells per μl, 50 cells per μl, 45 cells per μl, 41 cells per μl, 40 cells per μl, 35 cells per μl, 31 cells per μl, 30 cells per μl, 25 cells per μl, 21 cells per μl, 20 cells per μl, 18 cells per μl, 16 cells per μl, 15 cells per μl, 14 cells per μl, 12 cells per μl, 11 cells per μl, 10 cells per μl, 9 cells per μl, 8 cells per μl, 7 cells per μl, 6 cells per μl, 5 cells per μl, 4 cells per μl, 3 cells per μl, 2 cells per μl, 1 cell per μl, 0.9 cell per μl, 0.8 cell per μl, 0.7 cell per μl, 0.6 cell per μl, 0.5 cell per μl, 0.4 cell per μl, 0.3 cell per μl, 0.25 cell per μl, 0.20 cell per μl, 0.15 cell per μl, 0.1 cell per μl, 0.05 cell per μl, 0.01 cell per μl, and/or of any concentration range defined by any of these points, or any lower cell concentration. The ability to employ higher cellular concentration has many advantages. For example, if one can use 2, 3, 4, 5, 10, 20, 50, 100, 500, or even 1000 times the concentration of cells and therefore obtain 2, 3, 4, 5, 10, 20, 50, 100, 500, or even 1000 times the concentration of RNA in the RT-PCR reaction mixture, then this can provide a tremendous advantage in terms of speed, lower numbers of cycles, sensitivity, tolerance, and/or robustness of the RT-PCR reaction. These advantages could be significant to overcome any situations where the lysates and/RT-PCR reaction mixtures of the invention might not be as stable, from an RNA standpoint or as efficient from an RT-PCR standpoint, as prior lysates and/or RT-PCR reactions using lower cell concentrations.

Another advantage of some embodiments of the invention is that they can allow for highly efficient RT-PCR reactions using the methods and buffers of the invention, without the need for RNA isolation or sample preparation steps that require temperature variations and/or protein addition, DNA and/or protein precipitation in the sample, or long incubation times. One manner of measuring the efficiency of a real-time PCR reaction involves the determination of "Ct values." Ct refers to "Cycle Threshold." In real-time PCR, the amount of fluorescent signal is monitored after each cycle of PCR. Once the signal reaches a certain level, it has reached the "threshold." The Ct is the number of cycles of PCR that it took to reach that threshold of fluorescent signal. Thus, the lower the Ct value, the greater the concentration of nucleic acid target. For example, in the TaqMan® assay, typically each cycle almost doubles the amount of PCR product and therefore, the fluorescent signal should double if there is no inhibition of the reaction and the reaction was nearly 100% efficient with purified nucleic acid. In practice, if the Ct value produced by an RT plus reaction is at least 3 Ct values less than the Ct value from an RT minus reaction, the gDNA contribution to the Ct is less than ~12%. The lower the Ct value, the greater the signal. Thus, if the RT step is contributing cDNA in much greater excess than the gDNA, then you should observe a lower Ct value in the RT plus reactions. Every 3 cycles is about an 8-fold (2×2×2) difference in signal. Thus, if the RT plus reaction is 3 cycles lower than the RT minus, then there was about 8-fold more cDNA than genomic DNA (gDNA). In the context of the invention, benefits can be realized when the methods and buffers result in any difference in Ct value between an RT plus reaction and an RT minus reaction where all other components are held equal or substantially equal. For example, in some embodiments of the invention, differences in Ct values of 1, 2, 3, 4, 5, 6, 7, 8, 9, 10 or more (RT(−)-RT(+)), or any range derivable between any two of these points, will be possible and beneficial. Also, given the ease of the preparation of the RNA-containing samples for RT-PCR according to the invention, the invention can provide benefits even if it results in an RT-PCR reaction with a Ct value that is greater than a comparable RT-PCR reaction run on an identical RNA-containing sample that has been prepared by a more laborious procedure. For example, even if the Ct value of an RT-PCR reaction on an RNA-containing sample is 1, 2, 3, 4, or more times higher than that for an RT-PCR reaction on an RNA-containing sample produced by more laborious means, the lower efficiency of the RT-PCR reaction of the invention may be more than compensated for by the easy, more efficient sample preservation of the invention. This may be particularly true in cases of automation of RT-PCR, where the ability to quickly prepare samples for RT-PCR with one step at room temperature or a constant temperature may outweigh the need for additional amplification cycles.

In some embodiments, the methods of the invention further comprise analyzing amplified DNA to determine the presence of and/or quantity of an RNA in the biological unit. There are many reasons that one might wish to do this, including but not limited to determining gene expression patterns for research, diagnostic, pharmacogenomics, and therapeutic applications. In many cases, these methods will comprise admixing an RNA control with the reaction mixture or the at least a portion of the extract prior to reverse transcription. Such an RNA control can be employed as an internal standard for quantifying the RNA in the biological unit and/or as an exogenously added positive control to assure that the reaction mixture is functioning properly. Of course, controls such as RNA or DNA controls can also be added to the reaction mixture prior to an amplification procedure, and it is also possible to use RNA or DNA controls and external standards or positive controls in the context of the invention. Those of skill understand that there are a wide variety of manners in which to employ controls in the context of the invention, and will be able to employ appropriate such controls for any specific format that they are practicing.

In some embodiments, the invention may be employed to determine differences in RNA levels between biological units comprised in two or more samples. Skilled molecular biologists understand that there are a wide variety of contexts in which such analysis may be employed. For example, they may be employed to study differences in gene expression during development, differences in gene expression between normal and diseased tissues, or differences in gene expression due to the contacting of a biological unit with some form of nucleic acid, protein, small molecule, antibody, or other substance. In some embodiments, the invention relates to methods of determining whether or not an siRNA with which the biological unit has been contacted has altered the concentration of one or more RNA in the biological unit. Such embodiments may comprise comparing the presence of and/or quantity of cDNA products from the biological unit contacted with the siRNA with cDNA products obtained from a biological unit not contacted with an siRNA or contacted with a negative control siRNA. Such methods also embody the determining of whether or not a compound with which the biological unit has been contacted has altered the concentration of one or more RNA in the biological unit, and may optionally comprise comparing the presence of and/or quantity of cDNA products from the biological unit contacted with the compound with cDNA products obtained from a biological unit not contacted with the compound or contacted with a control.

There are a wide variety of techniques that can be used to detect RNA or DNA generated by the methods of the invention and, in many embodiments, determining the presence of and/or quantifying RNA. For example the invention contemplates, but is not limited to, the use of a labeled probe or intercalating dye to determine the presence of and/or quantify the RNA. Labeled probes are typically nucleic acids that comprise one or more detectable labels. Such labels can be visual, fluorescent, chemical, enzymatic, or radioactive labels, or any other label suitable for the practice of the invention. Such labels can be detected by methods that are well known to those of skill in the art. In particular, some embodiments of the invention involve the use of dual-labeled fluorescent probes, such as TaqMan® Gene Expression Assays (Applied Biosystems), Scorpion™ (DxS; Manchester, UK), LUX™ (Invitrogen); Ampliflour™ (Chemicon), or molecular beacon probes. In other particular embodiments, the invention involves the use of intercalating dyes, including but not limited to SYBR® Green and ethidium bromide.

Some embodiments of the invention comprise amplifying RNA from the lysate or admixture. There are many cases where researchers have a limited amount of sample and the RNA isolated from the sample is not enough to perform the desired assay, and those of skill will be able to employ the invention in any such cases. A technique to which this often applies is in producing a labeled nucleic acid from the isolated RNA and then hybridizing the labeled nucleic acid to a microarray. The signals produced at each of the addresses of the microarray indicate the level of expression for each of the genes on the array. Thus, a snapshot is taken of the abundance for each of the genes probed by the array.

Of course, the lysates and admixtures of the present invention may be used in almost any molecular biology technique involving the use of a biological unit lysate or admixture. Therefore, even though the lysates provide particular benefits in RNA-based techniques, the invention is not limited to such techniques. For example, the methods of using the lysates of the invention may comprise detecting one or more proteins in the lysate or admixture or a portion thereof. In some embodiments, protein detection may be used in combination with the practice of one of the RNA-based techniques discussed above, for example to determine or confirm whether differences detected in RNA or levels between samples are also detectable in protein levels in the samples. Proteins can be detected in any manner known to those of skill. In some examples, the protein is detected in an antibody-based assay, for example but not limited to immunoblotting, ELISA, or immunoprecipitation.

One advantage of the lysates and admixtures of the invention lies in their ability to stabilize RNA from significant degradation until such time as an RNA-based protocol can be performed. It is particularly beneficial that these lysates and admixtures are able to prevent significant RNA degradation for a relevant period at ambient temperatures typically found in laboratories. For example, it is possible for RNA degradation to be prevented at temperatures between 15° C. and 30° C., which are the far limits of most ambient lab temperatures. In many embodiments, the temperature will be room temperature, which is typically around 21° C., but may vary within labs. Of course, it is not required that the lysates and admixtures be stored at ambient temperatures. They may be stored at any temperature that allows for preservation of the RNA. For example one may store the lysates and admixtures at, −80° C., −20° C., 0° C., 4° C., 10° C., 15° C., 20° C., 21° C., 25° C., 30° C., 35° C., 37° C., 40° C., 45° C., 50° C., or within any range of temperatures defined by any two of these individual points.

Additionally, it is not necessary for the RNA to be protected from degradation forever. Rather, the objectives of many aspects of the invention may be realized so long as the RNA is protected from substantial degradation for enough of a period of time to allow for the desired assay or protocol to be performed. "Substantial degradation," may be defined as RNA degradation sufficient enough to effect the results of a desired assay or protocol. In some cases, "substantial degradation" does not occur so long as at least 5%, 10%, 20%, 25%, 30%, 40% 50%, 60%, 70%, 75%, 80%, 85%, 90%, 95%, 96%, 97%, 98%, 99%, and/or 100% of the RNA is preserved in the form of full-length sequences and/or transcripts. Of course, any range of percentage of preservation derivable between any of these points is also considered within the scope of these embodiments of the invention. Those of skill will understand that there are any of a variety of molecular biological techniques that can be employed to measure degrees of RNA degradation and/or preservation. For example, it is possible to use a 2100 BioAnalyzer (Agilent) as described below to determine intactness of RNA. The BioAnalyzer, and comparable devices may be employed to the ratio of 28S rRNA to 18S rRNA as an indication of intactness, with a ratio of between 1.0 and 2.0 to indicate that the RNA is relatively intact, with higher ratios indicating a greater level of intactness. This is because 28s rRNA is less stabile than 18s rRNA. In some embodiments of the invention, the ratio will be between 1 and 2. For example, the ratio may be 1.0, 1.05, 1.1, 1.2, 1.3, 1.4, 1.5, 1.6, 1.7, 1.8, 1.9, or 2, or any range derivable between any of these points. Additionally, the 2100 BioAnalyzer can be used to determine an RNA integrity number (RIN), as described in various places in the Agilent literature. The RIN is a number between 1 and 10, wherein 10 relates to completely undegraded RNA and 1 relates to completely digested RNA. In the context of some embodiments of the invention, the RIN will be 4, 5, 6, 7, 8, 9, 10 or any range derivable between these points.

Additionally, it is possible to evaluate RNA stability under a variety of storage conditions in terms of its ability to be used in a standard biological procedure, for example but not limited to real-time PCR.

In many embodiments, the lysate, or a portion thereof, will be employed in a protocol very quickly, i.e., within minutes, hours, or a day after preparation of the lysate or admixture. Therefore, the RNA will only need to be protected for a short amount of time. However, even in these embodiments, the invention provides benefits in that it allows for ambient temperature lysis and assurance that RNA degradation is not occurring. Further, in some embodiments, RNA in lysates and admixtures may be substantially protected from degradation for 1, 2, 3, 4, 5, or 6 days, 1, 2, 3, or 4 weeks, a number of months, a year, or more. Further, any range derivable between any of these time points is contemplated by the invention. Additionally, any combinations of specific points or ranges of temperature, level of preservation, and/or times of preservation derivable from the above are contemplated by the invention. For example, but not limited to: 85% RNA preservation for at least 2 hours, at 15-30° C.; a ratio of 28S rRNA to 18S rRNA of between 1.0 and 2.0, for at least 4 hours, at ambient temperature; and/or sufficient RNA preservation to allow for real-time PCR, or any other molecular biology procedure requiring intact RNA, for any of the above-described amounts of time at ambient temperature.

While the ability to maintain the stability/intactness of RNA in the lysate is one of the benefits of many of the preferred buffers and methods of the invention, those of skill will recognize that integrity of RNA is important in some, but certainly not all applications, such as RT-PCR applications where an oligo(dT) is used to prime the RT and the probe is far from the 3' end. In other cases, it is not necessary to have such a level of intactness or RNA stability. For example, RNA contained in lysates and admixtures according to the invention that have 0% full length RNA, can be used in embodiments of the invention such as one-step quantitative RT-PCR where gene specific primers are used for RT priming. The invention still has benefit even if the RNA is substantially degraded, so long as the degradation does not change the ability to perform a desired assay. For example, low pH lysis substantially increases the concentration of the sample, lysate, and/or admixture that may be used in the RT-PCR. The inventors have found that cells lysed at pH 7.0 lose linearity of signal earlier than cells lysed at a lower pH. Further, the precision and/or robustness of methods employed with low pH samples appears to be greater.

Temperatures of the lysate or admixture at the time of preparation may be at any temperature that is effective between 0° C. and 100° C. Typically, preparation occurs between 0° C. and 50° C., with between 15° C. and 37° C. preferred, and ambient temperature most preferred simply from the standpoint of simplicity.

Some embodiments of the invention further comprise adding an RNase inhibitor to the admixture. For example, the RNase inhibitor is a non-proteinaceous RNase inhibitor, such as ADP or a vanadyl complex. Proteinaceous inhibitors could also be used such as placental ribonuclease inhibitor or antibodies that inactivate specific ribonucleases. Other RNase inhibitors include a variety of small molecules. A listing of a wide variety of RNase inhibitors, which may be used alone or in combination with other inhibitors in the context of the invention may be found in U.S. patent application Ser. No. 10/786,875 entitled "Improved Nuclease Inhibitor Cocktail" by Latham et al., filed on Feb. 25, 2004, which is a continuation-in-part application of co-pending U.S. application Ser. No. 10/675,860 filed Sep. 30, 2003, which is a continuation of application Ser. No. 09/669,301 filed Sep. 25, 2000, now U.S. Pat. No. 6,664,379, which claims the benefit of U.S. Provisional Application No. 60/155,874, filed Sep. 24, 1999. The entire text of each of the foregoing applications is specifically incorporated herein by reference without disclaimer.

In some particular embodiments, the invention relates to methods of assaying RNA comprising: obtaining at least one biological unit containing RNA or sample comprising RNA not comprised in a biological unit; obtaining a low pH buffer; mixing the biological unit and the buffer to prepare a low pH lysate or mixing the sample and the buffer to prepare an admixture; and assaying RNA in the reaction mixture. These methods may then involve any analysis of RNA known to those of skill in the art or described herein. Some preferred embodiments comprise adding at least a portion of the lysate or admixture to a composition comprising reverse transcriptase to form a reverse transcriptase reaction mixture and incubating the reaction mixture under conditions resulting in a reverse transcription reaction to prepare cDNA. These embodiments may further comprise amplifying cDNA products of the reverse transcription reaction. Additionally, the embodiments may comprise determining the presence of and/or quantity of an RNA in the biological unit. For example, such detection may comprise use of a labeled probe or intercalating dye to determine the presence of and/or quantify the RNA.

In other embodiments, the invention relates to kits for assaying RNA in a biological unit or sample comprising RNA not comprised in a biological unit comprising, in one or more suitable container(s): a low pH buffer, high pH buffer, or RNA precipitating buffer; a reverse transcription buffer; reverse transcriptase; and dNTPs. Such kits may also comprise an RNA control. Additionally, such kits may comprise a thermostable DNA polymerase. The kits may also comprise an RNase inhibitor. The kits may also include primers and probes for the control RNA. They may further comprise a PCR buffer for an RT-PCR reaction and/or oligo dT or random primers for the reverse transcription step.

The invention also relates to buffers comprising a strong-weak acid, which are used in the context of the methods and kits described herein. To create some preferred buffers, with a buffer strength of ~10 mM centering around pH 2.5, preferably strong-weak acids of pKa<3 to 4, for example pKa 1 to 4 are employed. For example, chloroacetic acid (pKa=2.9), L-arginine (pKa=1.8), glycine (pKa=2.4); maleate (pKa=2.0); acetic acid (pKa=4.8); N-acetylalanine (pKa=3.7); β-acetylaminopropionic acid (pKa=4.4); N-acetylglycine (pKa=3.7); alanine (pKa=2.3); 2-aminobenzenesulfonic acid (pKa=2.5); 3-aminobenzenesulfonic acid (pKa=3.7); 4-aminobenzenesulfonic acid (pKa=3.2); 3-aminobenzonic acid (pKa=4.8); 4-aminobenzonic acid (pKa=4.9); 2-aminobutyric acid (pKa=2.3); 4-aminobutyric acid (pKa=4.0); 2-amino-3-methylpentanoic acid (pKa=2.3); 2-amino-2-methylpropionic acid (pKa=2.4); 2-aminopentanoic acid (pKa=2.3); 3-aminopropionic acid (pKa=3.6); arginine (pKa=1.8); barbituric acid (pKa=4.0); benzoic acid (pKa=4.2); bromoacetic acid (pKa=2.9); 3-bromobenzoic acid (pKa=3.8); 4-bromobenzoic acid (pKa=4.0); bromopropynoic acid (pKa=1.9); 3-tert-butylbenzoic acid (pKa=4.2); 4-tert-butylbenzoic acid (pKa=4.4); 2-butyric acid (pKa=2.6); butyric acid (pKa=4.8); N-carbamoylalanine (pKa=3.9); N-carbamoylglycine (pKa=3.9); 3-chlorobenzoic acid (pKa=3.8); 4-chlorobenzoic acid (pKa=4.0); chloropropynoic acid (pKa=1.85); citric acid (pKa=3.1; 4.8); cyanoacetic acid (pKa=2.5); 2-cyano-2-methylpropionic acid (pKa=2.4); dimethylmalonic acid (pKa=2.2); dimethylbenzoic acids (pKa=3.4-4.3); 2-ethylbutyric acid (pKa=4.8); fluoroacetic acid (pKa=2.6); formic acid (pKa=3.8); 2-furancarboxylic acid (pKa=3.2); glycerol-phosphoric acid (pKa=1.3); glycolic acid (pKa=3.8); glycylasparagine (pKa=2.9); N-glycylglycine (pKa=3.1); hexanoic acid (pKa=4.9); 4-hydroxylbenzoic acid (pKa=4.6); 2-hydroxy-1-naphthoic acid (pKa=3.3); 2-hydroxypropionic acid (3.9); 2-hydroxysuccinic acid (pKa=3.5); iodoacetic acid (pKa=3.2); isoleucine (pKa=2.3); isopropylmalonic acid (pKa=2.4); lactic acid (pKa=3.9); leucine (pKa=2.3); methyl benzoic acids (pKa=4.3-4.4); 3-methylbutyric acid (pKa=4.8); 4-methylpentanoic acid (pKa=4.8); 2-methylpropionic acid (pKa=4.9); nitrilotriacetic acid (pKa=1.7, 3.0); 4-nitrobenzoic acid (pKa=3.4); nitrous acid (pKa=3.4); norleucine (pKa=2.3); oxalic acid (pKa=4.3); pentanoic acid (pKa=4.9); phosphoric acid (pKa=2.2); o-phthalic acid (pKa=2.9); proline (pKa=2.0); propenoic acid (pKa=4.3); N-propionylglycine (pKa=3.7); propynoic acid (pKa=1.9); serine (pKa=2.2); succinic acid (pKa=4.2); sulfuric acid (pKa=2.0); sulfurous acid (pKa=1.9); tartaric acid (pKa=3.0); 2,3,5,6-tetramethylbenzoic acid (pKa=3.5); threonine (pKa=2.1); o-toluidine (pKa=4.3); 1,2,4-triazole (pKa=2.4); 2,4,6-trimethylbenzoic acid (pKa=3.4); trimethylsilylbenzene acids (pKa=4.1-4.2); (3-ureidopropionic acid (pKa=4.5); and/or valine (pKa=2.3) may be employed in the invention. Of course, combinations and derivatives of these acids can be employed. Currently, arginine, glycine, and chloroacetic acid may be employed in preferred embodiments.

The buffer may comprise a detergent, for example a non-ionic detergent such as Triton X-100, NP 40, or Tween 20; an anionic detergent, for example, sodium dodecyl sulfate (SDS) or sodium n-dodecyl benzene sulfonate; or a cationic detergent such as cetyl trimethyl ammonium bromide (CTAB).

In other embodiments, the invention relates to the substitution of high pH buffers and high pH lysates and admixtures for low pH buffers and low pH lysates and admixtures in all of the embodiments of the invention described above. As shown in the examples, such high pH embodiments allow for the realization of many of the same benefits as low pH embodiments. In this regard, the invention relates to methods comprising: obtaining at least one biological unit containing RNA or sample comprising RNA not comprised in a biological unit; obtaining a high pH buffer; preparing an admixture of the biological unit and the buffer; and lysing the biological unit in the buffer or adding the buffer to a sample comprising RNA not comprised in a biological unit to form a high pH biological unit lysate or sample admixture. In some embodiments, the high pH biological unit lysate or admixture has a pH of from 9 to 14. More preferably, the high pH biological unit lysate or admixture has a pH of greater than or equal to 11 and less than 14. These embodiments may further comprise adding at least a portion of the lysate or admixture to a composition comprising reverse transcriptase to form a reverse transcriptase reaction mixture and incubating the reaction mixture under conditions resulting in a reverse transcription reaction. In such cases, the reverse transcriptase may be comprised in a reverse transcriptase buffer that adjusts the pH of the reaction mixture to a level suitable for reverse transcriptase function. In this case, the pH of the reaction mixture can be between 7.0 and 9.5, more preferably, based on the type of reverse transcriptase employed, the pH is between about 8.0 and 8.4. The invention also encompasses kits comprising such high pH buffers, as well as the buffers themselves.

In addition to preserving RNA, the buffers and methods of the present invention can be used to preserve other types of nucleic acids, including DNAs, PNAs, etc.

As used herein the specification, "a" or "an" may mean one or more. As used herein in the claim(s), when used in conjunction with the word "comprising", the words "a" or "an" may mean one or more than one. As used herein "another" may mean at least a second or more. As used herein, the phrase "at least one" means one or more.

DESCRIPTION OF ILLUSTRATIVE EMBODIMENTS

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

A Basic Procedure for Cells Derived from Tissue Culture

HeLa and K562 cells are used as exemplary cell types that are suitable for treatment using the compositions and methods described herein. However, the invention is in no way limited to the exemplary cell types. It is expected that the compositions and methods apply to all cell types. One of ordinary skill would, in light of the disclosure, expect all other cells types to be amenable to the methods of the present invention.

To demonstrate the basic methods for cells derived from tissue culture, HeLa cells (adherent) were grown in Dulbecco' s Modified Eagle Medium (Invitrogen Corp., Cat. #10569-010) with 10% fetal bovine serum (FBS; Invitrogen Corp. Cat. # 10082-147) in a tissue culture flask to 50 to 75% confluency. The medium was removed and then the cells were incubated with 0.05% trypsin in 0.53 mM EDTA for 10 minutes at 37° C. Trypsin was inactivated by suspending the cells in medium with 10% FBS. Human K562 cells (suspension) were grown to $5 \times 10^5$ to $1 \times 10^6$ cells/ml in DMEM with 10% FBS in a T-75 flask. HeLa and K562 cell concentrations were determined with a hemacytometer and then 1 million cells were centrifuged at 3000 rpm for 5 minutes. The medium was removed and the cells were washed once with 1 ml of cold phosphate buffered saline (PBS). The cells were suspended in 100 µl of PBS to obtain a stock solution of 10,000 cells/µl. A five-fold serial dilution of the stock solution with PBS was carried out to give 10000, 2000, 400, 80 and 16 cells/µl. 10 µl of each dilution were added to 90 µl of buffer [10 mM L-Arginine, 16 mM HCl, 1% Triton X100, pH 2.5±0.2] at room temperature such that the final concentrations in the lysate were equivalent to 1000, 200, 40, 8, and 1.6 cells/µl in lysis solution (all specific examples in this specification use this buffer composition in the preparation of cell lysates and/or biological fluid admixtures, unless otherwise specified). The lysates were either incubated at room temperature for 1 to 2 minutes after a brief vortexing or gently shaken. 2 µl of the Control RNA (10 pg/µl) were spiked in 100 µl of the cell lysate as a positive control. The Control RNA primers and probe sequences were as follows: Forward primer, 5'-GCTCAATAATCGCCTCACTTGTG-3' (SEQ ID NO. 1); Reverse primer, 5'-CAACAAAGGGTACTCGTC-TATACTATATAAGC-3' (SEQ ID NO. 2); TaqMan Probe: 5'-(FAM)-TAGCCAGGCGTTTCCCGCGTTT-(TAMRA)-3' (SEQ ID NO. 3).

One Step RT-PCR (Reverse Transcription Followed by the Polymerase Chain Reaction in the Same Reaction Mixture)

A 1× master reaction mixture for RT-PCR (10 µl reaction volume in a 384 well PCR plate) is prepared with 1 µl of 10×RT buffer (500 mM Tris pH8.3, 750 mM KCl, 50 mM $MgCl_2$, 50 mM DTT), 1.6 µl of dNTP mix (2.5 mM each), 0.2 µl of 50×ROX standard [5 mg of ROX succinimide ester (Molecular Probe, Cat. #C-6125) dissolved in 0.5 ml DMSO; dissolve 7.5 mg glycine (100 µmoles) in 5 ml 0.1 M Sodium Bicarbonate, pH 8.2; add the ROX ester to the bicarbonate, wrap tube in foil, rotate at room temperature, 12-18 hours; quench by adding the entire sample to 24.5 ml of 20 mM Tris-Cl pH8.4, 0.1 mM EDTA, 0.01% Tween 20. This is a 500× stock. Dilute to a 50× solution in of 20 mM Tris-Cl pH 8.4, 0.1 mM EDTA, 0.01% Tween 20. Store at −20° C.], 0.1 µl (40 U/µl) of placental RNase inhibitor (RIP; Ambion, Inc. Cat. #2687), 0.4 µl of mixture of gene specific primers (10 µM each of forward and reverse) and TaqMan probe (2 µM), 0.08 µl (5 U/µl) of SuperTaq polymerase (Ambion, Inc. Cat. #2050 or 2052), 0.1 µl of MMLV-RT (100 U/µl, Ambion Inc. Cat. #2043 & 2044) and Nuclease-free water (Ambion, Inc. Cat. #9937) to 7 µl. For each 10 µl RT-PCR, the final concentration of each of the components are 50 mM Tris (pH 8.3), 75 mM KCl, 5 mM $MgCl_2$, 5 mM DTT, 0.4 mM each dNTP, 1×ROX standard, 0.4 U/µl RIP, 400 nM reverse and forward primers, 80 nM TaqMan probe, 0.04 U/µl SuperTaq and 1 U/µl MMLV-RT. In a 384-well plate, 3 µl of each cell lysate dilution from above is added to 7 µl of the master reaction mixture on ice such that the final cell concentrations in the RT-PCR reactions are 300, 60, 12, 2.4 and 0.48 cells/µl. Control reactions are included that do not include reverse transcriptase or any template by adding nuclease-free water. They should not generate any detectable signal if primers were designed to span intron(s) and no pseudogenes are present for the target gene. The samples were processed in a Prism 7900HT Sequence Detection System (Applied Biosystems, #4329002) and the following profile run: 42° C., 15 minutes; 95° C., 5 minutes; [95° C., 15 seconds; 60° C., 60 seconds]× 40 cycles.

These studies employed the Human CDC-2 (Cell Division Cycle) gene. Of course, any gene may be employed in regard to the methods discussed herein. Human CDC-2 primer and probe sequences were employed as follows: Forward primer, 5'-CCAGAAGTGGAATCTTTACAGGAC-3' (SEQ ID NO. 4); Reverse primer, 5'-CAAGTTTTTGACATGGGATGCT- 3' (SEQ ID NO. 5); and TaqMan probe: 5'-(FAM)-TACATTTCCCAAATGGAAACCAGGAAGC-(TAMRA)-3' (SEQ ID NO. 6).

CDC-2 was detected by real-time PCR. These CDC-2 primers did not span introns. For this reason, the reverse transcriptase minus reactions produced Ct values 5-7 units higher compared to reverse transcriptase plus reactions, indicating the detection of the CDC-2 sequence in the genomic DNA (gDNA). Ct refers to "Cycle Threshold." In real-time PCR, the amount of fluorescent signal is monitored after each cycle of PCR. Once the signal reaches a certain level, it has reached the "threshold." The Ct is the number of cycles of PCR that it took to reach that threshold of fluorescent signal. Thus, the lower the Ct value, the greater the concentration of nucleic acid target. In the TaqMan assay, typically each cycle almost doubles the amount of PCR product and therefore, the fluorescent signal should double if there is no inhibition of the reaction and the reaction was nearly 100% efficient with purified nucleic acid.

CDC-2 was detected in all cell strains tested: HeLa, K562, MCF-7, SKNAS, and NHDF-neo (a primary cell line). A plot of the Ct values against cell lysate concentrations was linear up to 1000 cells/µl. CDC-2 signal was readily detected at cell lysate concentrations greater than 1000 cells/µl, but the signals were no longer linear due to an inhibitory effect attributed to the higher cell concentrations. In addition, the Ct value for the control RNA was unchanged in all of the cell concentrations up to 1000 cells/0 indicating that there was no inhibition up to 1000 cells/µl. Above 1000 cells/0, the Ct values were higher, indicating that the cell lysates and admixtures were creating an inhibitory effect.

Two-Step RT-PCR

For each cell lysate, a 20 µl reverse transcription (RT) reaction was assembled with 2 µl 10× RT buffer (500 mM Tris [pH 8.3], 750 mM KCl, 50 mM MgCl$_2$, 50 mM DTT), 2 µl of random primers or oligo d(T)$_{18}$ (both at 50 µM), 4 µl dNTP mix (2.5 mM each), 1 µl RIP (10 U/0) (Ambion, Inc. Cat. #2687), and 1 µl of MMLV-RT (25 U/0) and 4 µl of RNase-free water (Ambion, Inc., Cat. #9937). As prepared above, 6 µl of each cell lysate dilution was added to 14 µl of the RT reaction and the reaction was incubated at 42° C. from 15 minutes to 60 minutes to synthesize cDNA. The reverse transcription reaction was incubated at 92° C. for 10 minutes to inactivate the MMLV-RT. Control reactions were included that do not include reverse transcriptase (RT minus) or any template (template minus).

To perform PCR, 7.5 µl of the cDNA were combined with 0.2 µl of SuperTaq Polymerase (5 U/0) (Ambion, Inc., Cat. #2050), 2.5 µl 10× real-time PCR buffer (100 mM Tris HCl pH 8.3, 500 mM KCl, 8% glycerol, 0.1% Tween 20), 2 µl dNTP mix (2.5 mM each), 5 µl 25 mM MgCl$_2$, 1 µl of the primer pair (10 µM mixture of the forward and reverse primers) and 1 µl of the TaqMan® probe (2 µM), 0.5 µl 50×ROX Standard, 5.3 µl Nuclease-free water (Ambion, Inc.). Human CDC-2 was detected with the same primers and TaqMan probe sequences as above. The reactions were placed in an ABI 7700 Prism thermocycler and ran using following profile: 95° C., 5 minutes; [95° C., 15 seconds; 60° C., 60 seconds]×40 cycles.

CDC-2 was tested in duplicates and detected in all cell samples that included K562 cells. Ct values against cell concentrations was linear up to 1000 cells/µl. Of course, those of skill in the art will be able to readily adapt these Example 2

Exemplary Low pH Buffers of the Invention

Many of the embodiments of the present invention are based on low pH buffers for generating cell lysates and body fluid admixture that can be used directly in RT-PCR or other enzymatic reactions. Strong-weak acids are used to make a low pH buffer (about less than pH 3). At this low pH, nuclease activity derived from a cell lysate is substantially lessened.

In order to create enough buffer strength (~10 mM) centering around pH 3.0, the inventors decided to use strong-weak acids (pKa<3 to 4). Chloroacetic acid (Sigma-Aldrich, #40, 292-3), L-arginine (Sigma-Aldrich, #A8094) and glycine (Sigma-Aldrich, #G7403) were dissolved in water to 10 mM and the pH was adjusted with 1N HCl (Sigma-Aldrich, #H9892) to between pH 2 and 4. pH~2.5 was found to be optimal. All acids worked well and results were comparable. In considering toxicity and cost, L-arginine was selected for preferred use, although all the other acids assessed performed equally. Other strong-weak acids with pKa<5.0 will also work by the same principle.

Studies defining of low pH buffers able to function in the context of the invention were done as set forth in EXAMPLE 1. HeLa and K562 cells were harvested and cell lysates were prepared using lysis buffers comprised of the different strong-weak acids chloroacetic acid, L-arginine and glycine about pH 2.5.30% in volume of each cell lysate was added to one step real-time RT-PCR master reaction mix. In both cell lines, the mRNA of GAPDH and Rho-A were detected by real-time TaqMan PCR at each cell concentration up to 1000 cells/µl. Although the primer pair sets used in these reactions detected genomic DNA, the RT plus reactions were at least 6 Ct values fewer than the RT minus, indicating that the mRNA were detected in much greater abundance (at least greater than about 100-fold) than the genomic DNA sequences.

Human GAPDH primer and probe sequences were employed as follows: Forward 5'-CACCAGGGCTGCTTT-TAACTCT-3' (SEQ ID NO. 7); Reverse 5'-TGGAATCATAT-TGGAACATGTAAACC-3' (SEQ ID NO. 8); TaqMan probe: 5'-(FAM)-ATATTGTTGCCATCAATGACCCCTTCATTG-(TAMRA)-3' (SEQ ID NO. 9).

Human Rho-A Primer and Probe sequences were employed as follows: Forward 5'-AGGCTGGACTCGGAT-TCGT-3' (SEQ ID NO. 10); Reverse 5'-TCCATCACCAA-CAATCACCAGT-3' (SEQ ID NO. 11); TaqMan probe: 5'-(FAM)-CTGAGCAATGGCTGCCATCCGG-(TAMRA)-3' (SEQ ID NO. 12).

Those of skill will be able to use these, and other similar test methods to examine the suitability of other low pH buffers in the context of the invention without undue experimentation.

Example 3

The Invention Functions with Multiple Cell Lines

HeLa, MCF-7, K562, SKNAS, and NHDF-neo (a primary cell line) were grown to 50-75% confluency in appropriate growth media. The adherent cells were harvested by trypsin, suspended in growth medium and counted with a hemacytometer. Suspension cells were counted directly in their medium. One million cells of each type was collected and centrifuged at 2000×G for 5 minutes. The cells were washed with PBS (Ambion, Inc.) and pelleted again by centrifugation 3,000 rpm (2,000×G) for 5 minutes. The cells were suspended in 100 µl PBS and five 1:5 dilutions were made in PBS. Ten µl of each cell suspension was added to 90 µl buffer at room temperature for final cell concentrations of 1000, 200, 40, 8, and 1.6 cells/µl in the Buffer. Two µl of the positive control RNA at 10 pg/µl was included in 100 µl of each cell lysate. After vortexing, the room temperature cell lysate was used for one step real-time TaqMan RT-PCR (EXAMPLE 1).

In each cell line, mRNA of C-JUN, CDC-2, GAPDH, PKC-alpha, VEG-F and the added control RNA was detected by real-time RT-PCR at each cell concentration. A plot of the Ct values against cell concentrations was linear up to 1000 cells/µl. For primer pairs that could amplify genomic DNA, the MMLV-RT minus controls (RT minus) had significantly higher Ct values compared to RT plus reactions indicating that the RT-plus reactions were detecting mRNA and not just the genomic DNA. The positive control RNA generated a similar Ct value in all cell types from each cell lysate concentration indicating that there was no inhibition of the RT-PCR. CDC-2 and GAPDH primers and probe sequences were as in EXAMPLE 1.

Human C-JUN primer and probe sequences were employed as follows: Forward: 5'-ACGTTAACAGTGGGT-GCCAA-3' (SEQ ID NO. 13); Reverse: 5'-CCCCGACG-GTCTCTCTTCA-3' (SEQ ID NO. 14); TaqMan Probe: 5'-(FAM)-TCATGCTAACGCAGCAGTTGCAAACA-(TAMRA)-3' (SEQ ID NO. 15).

Human PKC-alpha primer and probe sequences were employed as follows: Forward: 5'-ACTCCACGGCGTCT-CAGGA-3' (SEQ ID NO. 16); Reverse: 5'-GCGCGCGAT-GAATTTGTG-3' (SEQ ID NO. 17); TaqMan Probe: 5'-(FAM)-CCAACCGCTTCGCCCGCAAA-(TAMRA)-3' (SEQ ID NO. 18).

Human VEG-F primer and probe sequences were employed as follows: Forward: 5'-GATCGAGTACATCT-TCAAGCCATC-3' (SEQ ID NO. 19); Reverse: 5'-CTCGT-CATTGCAGCAGCC-3' (SEQ ID NO. 20); TaqMan Probe: 5'-(FAM)-TGTGTGCCCCTGATGCGATGC-(TAMRA)-3' (SEQ ID NO. 21).

Example 4

Use of Methods without the DNase Treatment

RNA samples are commonly incubated with DNase I to degrade contaminating genomic DNA prior to using it for RT-PCR such that the PCR primers only amplify the cDNA and not the genomic DNA. In using this method, it is preferred that the signal derived from the genomic DNA should be almost or completely undetectable. The signal contributed by the genomic DNA is usually assessed by performing PCR, instead of RT-PCR, on the sample. This reaction is often referred to as the reverse transcriptase (RT) minus reaction. Since there is no reverse transcriptase in the reaction, only target DNA will be amplified. However, the DNase I strategy may be omitted if primers can be designed that only amplify cDNA or amplify cDNA in preference to the genomic DNA. It is often possible to design primers that anneal to sequences in exons spanning a large intron in the gene of interest if the genomic sequence of the gene is known. In using this strategy, the PCR product derived from genomic DNA will be much longer than the cDNA PCR product. The shorter cDNA PCR product is preferentially amplified usually to the extent that the genomic product is not detected. Thus, using this strategy, a DNase treatment is not required to prevent genomic DNA contamination. Primers and probes designed using this strategy are commercially available from TaqMan® Gene Expression Assays—M Type (Applied Biosystems). No amplification is detected in RT minus reactions (Example 11).

In practice, if the Ct value produced by an RT plus reaction is at least 3 Ct values less than the Ct value from an RT minus reaction, the genomic DNA contribution to the Ct is less than (~12%). Therefore, omitting the DNase treatment will not significantly affect the mRNA quantification. The lower the Ct value, the greater the signal. Thus, if the RT step is contributing cDNA in much greater excess than the genomic DNA, then one should observe a lower Ct value in the RT plus reactions. Every 3 cycles is about an 8-fold (2×2×2) difference in signal. Thus, if the RT plus reaction is 3 cycles lower than the RT minus, then there was about 8-fold more cDNA than genomic DNA.

Example 5

RNA Stability of Cell Lysates

RNA stability was measured from HeLa cells lysed in buffer and incubated at 5 minutes and 1, 2, 4, 8 and 24 h at room temperature (~21° C.). Concentrations of 1000, 200, 40, 8 and 1.6 cells/µl were assessed. One-step real-time RT-PCR was performed with CDC-2 and GAPDH as in EXAMPLES 1 and 2 from each lysate and compared with a fresh lysate. No significant changes in Ct values were observed over the 24 hour period indicating that the intactness of the RNA was sufficiently maintained to generate equally sensitive signals.

In another study to directly assess intactness, RNA was isolated using the RNAqueous kit (Ambion, Inc., Cat. #1912) directly from HeLa cells and from cells disrupted with the buffer at 1000 cells/µl as above. The purified RNA was fractionated in an RNA LabChip (Caliper) using the 2100 Bio-Analyzer (Agilent). The ratio of the 28S rRNA to 18S rRNA are an indication of the degree of RNA intactness. Ratios in a range from about 1.0 to 2.0 reflect that the RNA is relatively intact. The data from this analysis demonstrate that the RNA was substantially intact when stored at room temperature for 8 h but is somewhat degraded at the 24 h period. However, as noted above, the RNA at all time points produced equal signals by real-time RT-PCR.

The ratios of 28S to 18S rRNA as analyzed by the 2100 Bioanalyzer (Agilent) for RNA isolated from cells disrupted using buffer and stored at room temp (~21° C.) for 0 to 24 hr.

TABLE 1

| Cell Lysate | 24 h | 8 h | 4 h | 2 h | 1 h | 5 min | 0 h | RNAqueous |
|---|---|---|---|---|---|---|---|---|
| RNA Conc. (ng/ul) | 273.2 | 413.6 | 312.1 | 400.4 | 393.3 | 312.4 | 409.9 | 246.1 |
| rRNA ratio (28S/18S) | 0.42 | 1.00 | 1.03 | 1.18 | 1.38 | 1.34 | 1.50 | 1.80 |

Of course, those of skill will be able to test the RNA of any cell lysates or body fluid admixtures of the invention using these or similar studies.

Example 6

Long-Term Stability of the Cell Lysate

HeLa cell lysates of 1000, 200, 40 and 8 cells/µl were prepared as in EXAMPLE 1 and stored at −80, −20, 4° C. and room temperature (~21° C.) for one week, one month and two months. One-step real-time RT-PCR was performed with VEG-F (EXAMPLES 1 & 3) from each lysate and compared with a lysate made fresh. The real-time data showed no significant changes in signal for any storage conditions less than one month.

The RNA from lysates at 1000 cells/µl stored for one and two months and from cells freshly lysed were purified using RNAqueous and analyzed using the RNA LabChip and the 2100 Bioanalyzer (as in EXAMPLE 5). The profile of the RNA stored at −80° C. and −20° C. for two months was as intact as the RNA from a fresh lysate.

Example 7

Cells Preserved in RNAlater®

Compatibility of the invention was tested with cells stored in RNAlater®(Ambion Inc. Cat. #7020). RNAlater® is a solution that protects RNA from degradation in cells and tissues. An experiment was performed first to see if RNAlater® needed to be washed from the cells before lysing. Cells were washed once with cold PBS and then suspended in cold PBS and stored on ice. Two samples of $2\times10^6$ HeLa cells were suspended in 200 µl RNAlater® for 2 h on ice. After 2 h, one sample was washed, suspended and diluted with PBS to 32 to 20,000 cells/µl. The other sample was diluted in RNAlater® to 32 to 20,000 cells/µl. Cell lysate was made by adding 5 µl of the cells to 95 µl of lysis buffer for one-step RT-PCR (EXAMPLE 1). CDC-2, GAPDH, VEG-F and PKC-α one-step, real-time RT-PCR were performed in duplicate on each cell lysates with lysate concentrations of 1000, 200, 40 cell, 8 and 1.6 cells/µl (EXAMPLES 1, 2 and 3). Cells taken directly from RNAlater for cell lysis did not generate signal whereas those cells stored in RNAlater, washed in PBS and then subjected to cell lysis generated a strong signal in real-time RT-PCR.

Cells stored in RNAlater® 24 h at room temperature were then tested with the acid lysis protocol after washing with PBS. A total $2\times10^6$ HeLa cells were stored in 1 ml of RNAlater® at room temp for 24 h. The RNAlater® was removed by centrifuging the cells at 3000 rpm for 5 minutes at 4° C. The pelleted cells were suspended in PBS, and kept on ice. This was compared to cells lysed freshly. GAPDH and VEG-F one-step RT-PCR were performed in duplicate on cell lysates with lysate concentrations of 1000, 200, 40 and 8 cells/µl. There was no difference in signal among the differently treated samples.

Example 8

Use of Methods on siRNA Validation

Cells-to-Signal can be used to measure the siRNA knockdown of gene expression. siRNA are ~21 base pair double-stranded RNAs that can be used to specifically target the degradation of an mRNA by transfecting these siRNA into a cell (Elbashir, 2001). 30000

HeLa or MCF-7 cells were seeded in each well of a 24-well culture plate (Nalge Nunc International, Cat. # 143982) in 450 µl of Dulbecco' s Modified Eagle Medium (DME; Invitrogen Corp., Cat. #10569-010) with 10% fetal bovine serum (Invitrogen Corp., Cat. #10082-147). Gene specific siRNAs (GAPDH, Ambion, Inc., Cat. #4605; RAF1, Ambion, Inc., Cat. #51197) and a negative control scrambled siRNA sequence (Ambion, Inc., Cat. #4605) were diluted in Opti-Mem to a 10× concentration to which 2 µl of Oligo-fectamine™ transfection reagent (Invitrogen, Cat. #12252-011) was added and incubated for 15 minutes at room temperature (~21° C.). 50 µl of the complex in OptiMem was then added to the cells. The cells were then incubated at 37° C. for 48 hrs. The medium was removed and the cells washed once with PBS. 500 µl of buffer was added to the transfected culture cells and the plates shaken for 5 minutes at room temperature. Each cell lysate was tested in one step real-time RT-PCR reaction for GAPDH, RAF and 18S rRNA in triplicate (EXAMPLE 1).

The expression levels of GAPDH and RAF were decreased by >80% by their respective gene specific siRNAs after normalization with 18S rRNA as assessed by RT-PCR. GAPDH levels in HeLa cells were decreased by 88% with 3 nM of its siRNA compared to 3 nM of scrambled negative control, while the expression of 18S rRNA was unchanged.

Human RAF1 primer and probe sequences were employed as follows: Forward: 5'-CCCCAACAATCTGAGCCCA-3' (SEQ ID NO. 22); Reverse: 5'-GGGTCCCAGATACTGGT-GCC-3' (SEQ ID NO. 23); TaqMan Probe: 5'-(FAM)-TCA-CAGCCGAAAACCCCCGTGC-(TAMRA)-3' (SEQ ID NO. 24).

Human 18S rRNA primer and probe sequences were employed as follows: Forward: 5'-TCAAGAAC-GAAAGTCGGAGG-3' (SEQ ID NO. 25); Reverse: 5'-GGA-CATCTAAGGGCATCACA-3' (SEQ ID NO. 26); TaqMan Probe: 5'-(FAM)-TGGCTGAACGCCACTTGTC-CCTCTAA-(TAMRA)-3' (SEQ ID NO. 27).

Example 9

SYBR Green Real-Time PCR

HeLa and K562 cells were processed with buffer to concentrations of 1000, 200, 40, 8 and 1.6 cells/0.2 µl of positive control RNA (10 pg/µl) was spiked into 100 µl of each cell lysate and into buffer without cells as in EXAMPLE 1. For two-step, real time RT-PCR, reverse transcription was carried out separately with either oligo dT primers or random decamers (EXAMPLE 1). Real-time PCR for CDC-2, GAPDH and control RNA was performed using the cDNA from the reverse transcription step (EXAMPLES 1 and 2).

SYBR Green (Molecular Probes, S-7563, 10000× concentration in DMSO) was first diluted 1:100 in water and 25 µl of it was added to 975 µl of 10×RT buffer (500 mM Tris pH 8.3, 750 mM KCl, 50 mM $MgCl_2$, 50 mM DTT) for a final dilution of 1:4000 in the RT buffer. A 1× master reaction mixture of 10 µl reaction is prepared with 1 µl of 10× real time buffer (100 mM Tris-HCl pH 8.3, 500 mM KCl, 8% glycerol, 0.1% Tween 20) with final 1:4000 diluted SYBR Green in it, 1.6 µl of dNTP mix (2.5 mM each), 0.2 µl of 50×ROX standard (see Example I), 0.1 µl (40 U/µl) of placental RNase inhibitor (Ambion, Inc. Cat. #2687), 0.4 µl of mixture of gene specific primers and TaqMan probe (10 µM of forward and reverse primers and 2 µM of the TaqMan probe), 0.08 µl (5 U/µl) of SuperTaq polymerase (Ambion, Inc. Cat. #2050 or 2052), 0.1 µl of MMLV-RT (100 U/µl, Ambion Inc. Cat. #2043 & 2044) and Nuclease-free water (Ambion, Inc. Cat. #9937) added to bring the volume to 7 µl. In a 384-well plate, 3 µl of each cDNA from the RT reaction is added to 7 µl of the master reaction mixture on ice. Place the samples in the Prism 7900HT Sequence Detection System (Applied Biosystems, Product #4329002) and run the following profile: 95° C., 5 minutes; [95° C., 15 seconds; 60° C., 60 seconds]×40 cycles with dissociation protocol.

Real-time PCR for CDC-2 and the positive control RNA were performed with their primers and probes on cDNA from the RT step (primer and probe sequences in EXAMPLES 1 and 2). The dissociation curves of the two-step SYBR Green RT-PCR from CDC-2 and the control RNA generated single peaks indicating gene specific products. Ct values for CDC-2 were linear ($R^2$=0.99) with log cell inputs for two cell lines tested (HeLa and K562) with either oligo(dT) priming or random decamer priming.

Example 10

Multi-Well Format for Gene Expression Analysis and Comparison of Methods to RNAqueous-MAG, an Established RNA Isolation Method Cells-to-Signal and an established RNA isolation method [RNAqueous-MAG, a 96-well Automated Kit (Ambion Inc. Cat. #1812)] were compared in a 96-well plate experiment. To demonstrate the utility of the invention in a multi-well format for gene expression analysis, 3000 HeLa cells were plated in 48 wells of a 96-well plate and 3000 MCF-7 cells were seeded in the other 48 wells and grown overnight in 0.2 ml DME medium with 10% FBS (Phenix, Cat. #TC-9296). For the Cells-to-Signal protocol, the medium was removed and the cells washed with 0.2 ml PBS. 200 µl of buffer was added to each well and the plate was shaken on a plate shaker at 60 rpm for 5 minutes at room temperature (~21° C.). For the RNAqueous-MAG protocol, a laboratory automation workstation (Biomek 2000, Beckman) was used and all processing steps were entered into it for automation. The final RNA product was eluted to 200 µl.

One step real-time RT-PCR to detect GAPDH and VEG-F was performed using the RNA purified from RNAqueous MAG and the cell lysates as templates, in a 384-well Plate (EXAMPLES 1, 2 and 3). In each sample, GAPDH and VEG-F was detected by real-time PCR. Ct values for GAPDH and VEG-F from HeLa and MCF-7 cells were almost identical between the two methods. The preparation of template by Cells-to-Signal was completed one hour faster than by the automated RNAqueous-MAG.

cific primers and TaqMan probe (10 µM of forward and reverse primers and 2 µM of the TaqMan probe) as described in EXAMPLE 1.

All of the TaqMan® Gene Expression Assays primers/probe sets were able to detect their respective mRNA from each cell lysate. RT minus reactions did not generate any detectable signal from the "M"-type assays whereas for the S-type, only C-JUN and PTP4A1 showed>5Ct difference between RT plus and RT minus reactions. For all other S types, Ct difference was only 1-3.

Example 12

Use of Methods on Whole Blood

Fresh blood was drawn using a Microtainer safety flow lancet (Becton Dickinson, Cat. # 366357). 1 to 20 µl of fresh finger-prick whole blood was transferred to a 1.5 ml nuclease-free microfuge tube (Ambion, Inc., Cat. #12400) with 20 µl pipet barrier tips (Ambion, Inc., Cat. #12645) and was lysed with buffer (EXAMPLE 1) containing the positive control RNA. 3 µl of the whole blood lysate was used for one-step real time RT-PCR. Both spiked control RNA and 18S rRNA were detected when up to 10 µl of whole blood was processed with 90 µl buffer.

Example 13

Use of Invention on Leukocyte Enriched Blood

Volumes from 6.25 µl to 100 µl of fresh human whole blood drawn by the finger-prick method were mixed with 1.2 ml of red blood cell (RBC) lysis solution (144 mM $NH_4Cl$, 1 mM EDTA, 1 mM $NaHCO_3$, pH 7.0), vortexed, and then incubated on ice for 5 minutes to preferentially lyse the red cells. The lysate was centrifuged for 5 min at 800×G

TABLE 2

| Gene | GAPDH (Ct Values) | | | | | | VEG-F (Ct Values) | | | | | |
|---|---|---|---|---|---|---|---|---|---|---|---|---|
| Method | RNAqueous-Mag | | | Cells-to-Signal | | | RNAqueous-Mag | | | Cells-to-Signal | | |
| Cell line | Ave Ct | St dev | CV % | Ave Ct | St dev | CV % | Ave Ct | St dev | CV % | Ave Ct | St dev | CV % |
| HeLa | 20.65 | 0.45 | 2.2 | 20.47 | 0.16 | 0.8 | 26.71 | 0.45 | 1.8 | 26.54 | 0.20 | 0.8 |
| MCF-7 | 21.90 | 0.24 | 1.1 | 22.08 | 0.20 | 0.9 | 27.92 | 0.24 | 0.86 | 28.2 | 0.29 | 1.0 |

Example 11

Compatibility of the Invention with TaqMan® Gene Expression Assays

TaqMan® Gene Expression Assays (Applied Biosystems) are pre-designed primers and probe sets for real-time TaqMan PCR. Two different types of primers and probe sets were tested: "M"-primers from multiple exons that are designed to eliminate signal from genomic DNA, and "S"-primers that hybridize to a single exon and may amplify genomic DNA.

HeLa cells were harvested and suspended in buffer to concentrations of 1000, 200, 40 and 8 cells/µl (EXAMPLE 1). One step, real-time TaqMan RT-PCR reactions were prepared with 10 different TaqMan® Gene Expression Assays including C-JUN (S), CDC-2 (M), ATP10 (S), GJA1 (S), KRT6B (S), MGAT2 (S), PTP4A1 (S), COL6A2 (S), BCL2 (S) and CCNA1 (M) as in EXAMPLE 1. Prepare 1× master reaction mixture of 10 µl reaction with 0.5 µl of the primers/probe mixture (20×) instead of the 0.4 µl gene speto pellet the leukocytes. The supernatant was removed and the enriched leukocytes were processed with 100 µl buffer (EXAMPLE 1). 3 µl of the leukocyte lysates were used for a 10 µl qRT-PCR to quantify C-JUN, Rho-A, VEG-F (EXAMPLES 2 and 3), alpha 1 hemoglobin (HBA 1) and beta hemoglobin (HBB). All genes were detected from the leukocyte lysates derived from 1 µl to 15 µl of whole blood. The Ct values were linear up to 10 µl whole blood or approximately 70,000 leukocytes.

Human HBA1 Primer and Probe sequences were: Forward primer, 5'-CGCCTCCCTGGACAAGTTC-3' (SEQ ID NO. 28); Reverse primer, 5'-GCTCCAGCTTAACGGTATTTGG-3' (SEQ ID NO. 29); TaqMan probe: 5'-(FAM)-TGGCTTCT-GTGAGCACCGTGCTG-(TAMRA)-3' (SEQ ID NO. 30).

Human HBB Primer and Probe sequences were: Forward primer, 5'-GCTGGCCCATCACTTTGG-3' (SEQ ID NO. 31); Reverse primer, 5'-CCAGCCACCACTTTCTGATAGG-3' (SEQ ID NO. 32); TaqMan probe: 5'-(FAM)-AGAAT-TCACCCCACCAGTGCAGGC-(TAMRA)-3' (SEQ ID NO. 33).

Example 14

Monitoring Effects of Drug Treatment with the Invention

HeLa cells were seeded DME media with 10% FBS in each of three wells in a 12-well tissue culture plate (Nalge Nunc International, Cat. #150628) at 125,000 cells/well. After an overnight incubation, phorbol myristate acetate (PMA) was added to final concentrations of 10, 1 and 0 nM in the growth medium. The cells were incubated at 37° C. for 24 hours. The medium was removed and the cells washed with PBS. The cells were incubated with 0.05% trypsin in 0.53 mM EDTA for 10 minutes at 37° C. to detach the cells. Cells were counted and concentration was determined. Cells were centrifuged at 800×g for 5 minutes. The medium was removed and the cells were washed once with PBS. Each cell pellet was suspended in PBS to obtain a stock solution of 10000 cells/µl. A five-fold serial dilution of the stock solution with PBS was carried out to give 10000, 2000 and 400 cells/0.10 µl of each dilution was added to 90 µl of Buffer at room temperature such that the final cell concentrations in the lysate were 1000, 200 and 40 cells/µl. The samples were gently shaken at room temperature (~21° C.) for 1 to 2 min. As in EXAMPLE 1, cell lysate of 30% of the final reaction volume was added to a one step real-time RT-PCR reaction with primers and TaqMan probe for tissue plasminogen activator (t-PA) and 18S rRNA (EXAMPLE 8). The t-PA primer and probe sequences were as follows: Forward primer, 5'-GGCGCAGTGCTTCTCTA-CAG-3' (SEQ ID NO. 34); Reverse primer, 5'-TAGGGTCTCGTCCCGCTTC-3' (SEQ ID NO. 35); TaqMan Probe: 5'-(FAM)-TTCTCCAGACCCACCACACCGC-(TAMRA)-3' (SEQ ID NO. 36).

```
Control RNA (1036 nt long artificial mRNA)
sequence:
                                       (SEQ ID NO. 37)
GGGAGAAGACUGCGGCAUAUAAGCGCUCAAUGGCCCUUACUUGUUGCCUA

GAUUAUAUUAAAGAUCCAUACGUUACCUGCCAACCGUCAACUCCCCGACG

UCCUUUACUUGAGAACAUCGAGCAAAUCUUCUGCCACCUAAGCGGCCGCA

GCCUAAAGAUUACUUAGUUCUGUUGGGUGCUGCAAUAACAACAAAGGGUA

CUCGUCUAUACUAUAUAAGCGCGAUAAUAUCUAGAAACGCGGGAAACGCC

UGGCUAGUCAUCGCACAAGUGAGGCGAUUAUUGAGCCAAUCAUCGGCGAU

UAACUUAAAGAAAAGCGGGUACGGGAUAUCGCUAUGUGCCGCGGCAAAGG

CUGCCAACAUAAAAUGUGCAAGCGUAAAUGCAGCGUCCAUGGUAAAAUUA

GUUUGAGCCUUGAUGUCUUAGAUGAUCCACUAAUCGGCUACCCUUGCUAG

UAGGUGUAGAUUCUCGAAAAGUCUUUUAGUAGGUGAUCCUCUGGUACGUC

AUAUAAUAUAUCUGCUCUAUAUAGCCACUUCCACGCUUAGAUCUCCGUGC

UCAUCACCAUCCGUAGAUCGUCGACCUCUCAUACUCUAGUCACUGUGGUG

UUCGUGGGUGCAGGUAUUGACAGGCUCAUACAUAUAAUAUGAAAUUGGGC

CUUCCGCAGCUCUGAACUAUCGAGCUUCCUUCUAAGAAUGAAUGUUGGGA

AGCCCGAUUUGAUAAACGCACGGCGCAAUAGCUAAACAGAUCUUAGGAGU

UUCACCACUGGAGUCAGCGUAAAUACACUGAUCUUGCGAAAAUAGUUGGC

GGUCUUAUAAACUGAGUAGAGCGCGCUUGCGUCCAAUACGAUUAGAUUCC

AACCGCGAUGCCACUAUGGCGUACAAAUAAGAAUGUUUUCAAGGGGAUAA

GAUGGAGUCAUCUGGCCGCGUAACCCUACAAAAAAAAUGAACCGUAAUAG

AGCAGUUGUACAUCGAGACGUACGUUGCACGAAAAAUAGUGACUUUACGU

CAGUACAAAAAAAAAAAAAAAAAAAAAAAAAAAAAAA
``` t-PA was detected by real-time PCR at all cell concentrations and PMA concentrations. As expected (Arts, 1997), the level of t-PA mRNA increased when the cells were grown in the presence of PMA (Table 3).

TABLE 3

| Leukocyte Lysate (cells/µl) | PMA (nM) | t-PA (fold increase compared to 0 nM PMA) |
|---|---|---|
| 1000 | 1 | 8 |
| 1000 | 10 | 39 |
| 200 | 1 | 9 |
| 200 | 10 | 62 |
| 40 | 1 | 16 |
| 40 | 10 | 147 |

Example 15

Use of the Invention with Fixed Cells

HeLa and MCF-7 cells grown to 80% confluency in DME media with 10% FBS were harvested and washed with PBS. The cells were then fixed using three different methods: formalin, paraformadehyde, or ethanol fixation. The cells were suspended in 1 ml of 4% formalin or paraformaldehyde in PBS. The cells were incubated on wet ice for 2 hours. For the ethanol fixation, the cells were subjected to a gradient fixation protocol. The cells were suspended in 75% ethanol at room temperature for 30 seconds then spun down and removed. The cells were then washed with 85% ethanol, followed by 95% and 100% at room temperature for 30 seconds. The cells were left in 100% ethanol for 1 hour on ice.

After the fixation, the cells were washed twice with 1 ml ice cold PBS, suspended in PBS and lysed with buffer. This was compared with cells that were not fixed. Cell lysates were used in one-step real-time RT-PCR at cell concentrations of 1000, 200, 40 and 8 cells/µl to detect GAPDH and VEG-F. Signals were detected for both genes in both cell lines, but for nearly all of the samples, the Ct values were higher for the fixed cells. However, this does indicate that fixed cells can be employed in at least some embodiments of the invention.

Example 16

Immunoblotting Using the Cell Lysate

Measuring protein concentrations is an important tool for RNAi experiments and it may become more important if miRNA or miRNA inhibitors are used to screen target gene expression, analyze pathways, identify antagonistic or cooperative miRNA effects or determine the optimal combinations of miRNA that regulate a given gene. Since the buffer does not contain any reagents that will degrade protein, the cell lysates may also be used for detecting protein by immunoblotting or ELISA. Thus, after a target mRNA was demonstrated to be up- or down-regulated by RT-PCR from a cell lysate, then the same cell lysate could be used to assay for the effect on the translated protein.

HeLa cells were transfected with siRNA for GAPDH or scrambled sequence siRNA (Ambion, Cat. #4605). 48 hours after transfection, the cells were processed with buffer to a concentration of 1000 cells/μl. Real-time RT-PCR was performed for the cells transfected with the scrambled and GAPDH siRNA. The cells transfected with the GAPDH siRNA had a decreased concentration of GAPDH mRNA. Additionally, 1 M TRIS pH 8.0 was used to raise the pH of the cell lysates, the protein concentration was assessed using a Bradford assay, 6×SDS PAGE loading buffer was added to the lysate and incubated at 95° C. for 3 minutes. The lysates were fractionated on a 10% acrylamide gel and then the proteins were transferred to nitrocellulose membrane. Using standard immunoblotting procedures, the immunoblot was probed using an anti-GAPDH antibody (Ambion, Cat. #4300) at 1:5000 in PBSTM (PBS, 0.05% Tween20, 5% non-fat dry milk) at 4° C. for overnight and an anti-mouse HRP antibody was used as the secondary antibody at 1:5000 in PBSTM, incubated for 60 minutes at room temperature (~21° C.). The blot was washed five times with PBST. Super-Signal® West Pico Chemiluminescent Substrate Kit (Pierce, Cat. #34080) was used for detection. The GAPDH protein was reduced in the cells transfected with siRNA compared to the transfected with scrambled sequence, correlating with the real-time RT-PCR data.

In some cases, the protein concentration of the protein to be analyzed may be near the limit of detection in the cell lysate. It is possible to increase the protein concentration by precipitating the protein from the cell lysate prior to immunoblotting. Such standard procedures known by those skilled in the art are acid precipitation (for example, with 10% trichloroacetic acid), ethanol precipitation, or acetone precipitation (e.g., see, http://www.ls.huji.ac.il/~purification/Protocols/ProteinPrecipitation.html).

Example 17

RNA Amplification

DNA microarrays enable scientists to assess the level of multiple different mRNAs in a biological sample at a specific point in time. By comparing the expression levels of different genes from biological samples derived from different tissues or subjected to different environmental conditions, it is possible to infer which genes are responsible for generating specific phenotypes. This process is called expression profiling.

Expression profiling typically requires that total RNA is isolated from the biological sample and then the RNA must be labeled, prior to its hybridization to the microarray. In many instances, the amount of RNA isolated from the biological sample is too low to be useful for this procedure and therefore, there are methods available for increasing the starting material. The MessageAmp™ kits (Ambion, Inc.; Cat. #1750 & 1751) are based on the procedure of Phillips (1996) and are used to representationally increase the absolute amount of a total RNA sample by over 100-fold, often 1000-fold and can be used to go as high as 1 million-fold. This procedure is also used to label an RNA sample with biotin or a fluorescent dye for the purposes of probing a DNA microarray. Typically, the starting material for amplifying RNA is a minimum of ~100 ng of total RNA from the sample. Briefly, the procedure is as follows. The RNA is reverse transcribed in the presence of an oligonucleotide primer that encodes an RNA polymerase promoter such as a T7 phage promoter. In the procedure by Kacian (U.S. Pat. No. 5,554,516), the material is transcribed by T7 RNA polymerase to synthesize RNA. In the procedure by Phillips (1996), a second strand of cDNA is produced and then the double-stranded DNA is transcribed by a phage polymerase.

Lysates and admixtures generated using the buffer will function in the MessageAmp procedure using the same cell concentrations in the RT step as used in real-time RT-PCR. This will be useful when a large number of samples are being prepared in a multi-well plate, especially for microarrays that are formatted in 96- or 384-wells plates (Gene XP Biosciences, BioGridArray).

Example 18

Use of Invention with an Alkaline Lysis Buffer

A comparison was made of the chloroacetic lysis buffer and the citric acid lysis buffer at pH 3.0. 10 mM of each was made with 1% Tx-100 and HCl was added to pH to 3.0. Another lysis buffer was made with 1 mM NaOH and 1% Tx-100 at pH 11.0. HeLa S3 cells were harvested and suspended and diluted in PBS. 10 μl of each cell suspension was added to 90 μl of each lysis buffer. The samples were lysed at 50° C. for 5 minutes. GAPDH was assayed by one-step qRT-PCR using 3 μl of lysate in a 10 μl reaction. The Ct values derived from the alkaline lysis were comparable to those of the acidic buffers (Table 4).

TABLE 4

| | Cells/μl of Lysate | | | |
| --- | --- | --- | --- | --- |
| | 10,000 | 1,000 | 100 | 10 |
| Chloroacetic Buffer | 13.30 ± 0.75 | 14.64 ± 0.11 | 17.02 ± 0.49 | 20.18 ± 0.26 |
| Citric Acid | 13.61 ± 0.85 | 15.98 ± 0.58 | 19.36 ± 0.70 | 21.61 ± 0.70 |
| 1 mM NaOH | 40.00 ± 0.00 | 17.08 ± 0.32 | 17.74 ± 0.11 | 20.31 ± 0.20 |

Example 19

Cellular Rna Protected and Precipitated in the Acidic Cell Pellet

To test if the acidic lysis buffer precipitates the cellular RNA in the acidic cell lysate, experiments were performed on HeLa cell lysates. 3×10$^6$ HeLa cells were harvested and washed once in PBS. The cells were suspended in 300 μl of PBS to a concentration of 10000 cells/μl and kept on ice as in EXAMPLE 1. Three sets of cell lysates were made by adding 20 μl of the cell suspension to 180 μl of acidic lysis buffer, a final concentration of 1000 cells/μl. The cell lysates were incubated for 2 min at room temperature and duplicates were centrifuged for 2 min at 13000 rpm while one set was not centrifuged as a control. Supernatants were carefully removed to new tubes. RNA from each pellet and supernatant as well as from the total cell lysate was purified using a silica filter based total RNA isolation kit with 10 μl of total elution (RNAqueous-Micro kit, Ambion, Inc. Cat. # 1927) and analyzed using the 2100 Bioanalyzer (Agilent). 1 μl of 100 ng of HeLa S3 total RNA (Ambion Inc. Cat. #7852) was used as a positive RNA control on the Agilent gel analysis. The RNA from each of the samples were intact. The majority of the RNA was in the pellets. The ratio ~3.5 comparing the quantity of the RNA in pellet to the supernatant (Table 5).

TABLE 5

| RNA purified from: | Total cell lysate | Pellet 1 | Supernatant 1 | Pellet 2 | Supernatant 2 | HeLa S3 total RNA (100 ng/µl) |
|---|---|---|---|---|---|---|
| RNA concentration | 294.15 ng/ul | 280.57 nl/ul | 72.56 ng/ul | 188.58 ng/ul | 55.13 ng/ul | 118.96 ng/ul |
| rRNA ratio (28S/18S) | 1.28 | 1.45 | 1.51 | 1.50 | 1.32 | 1.33 |

Example 20

Assaying RNA in Saliva, Plasma, and Other Body Fluids

Saliva, like other bodily fluids, has been used to monitor human health and disease. Li et al. (2004) demonstrated that human mRNA exists in cell-free saliva, and this indicates that salivary mRNA may provide potential biomarkers to identify populations and patients at high risk for oral and systemic diseases. This demonstrates that RNA can be isolated from the cell-free saliva supernatant and linearly amplified with RT-PCR. It is anticipated that other cell free bodily fluids will contain such mRNA as well, and that this mRNA will be amenable to amplification and other techniques. Further, Silva et al. (2002) determined the presence of plasma tumor RNA in patients with colon cancer patients, indicating that the methods and buffers of the invention can be used in context with plasma to assay for cancer and other disease states.

In this regard, the methods and compositions of the present invention will provide significant advantages by allowing for a streamlined collection then usage of bodily fluids comprising the use of buffers of the invention to stabilize RNA in body fluid samples.

For example, one will, in view of this specification, obtain a saliva, plasma, or other body fluid sample including but not limited to serum, urine, whole blood, sputum, fecal matter, or cerebral spinal fluid, mix the body fluid with a low pH, high pH, or RNA precipitating buffer to form a body fluid admixture, and then perform any RNA-based molecular biology procedure on the admixture. In particular, the studies and techniques performed above with cell lysates above can be performed with body fluid admixtures without undue experimentation.

REFERENCES

The following references, to the extent that they provide exemplary procedural or other details supplementary to those set forth herein, are specifically incorporated herein by reference.

U.S. Pat. No. 5,386,024
U.S. Pat. No. 5,399,491
U.S. Pat. No. 5,554,516
U.S. Pat. No. 5,554,516
U.S. Pat. No. 5,693,467
U.S. Pat. No. 5,891,636
U.S. Pat. No. 5,973,137
U.S. Pat. No. 6,316,608
U.S. Pat. No. 6,610,475
U.S. Pat. No. 6,664,379
U.S. patent application Ser. No. 09/160,284
U.S. patent application Ser. No. 09/815,577
U.S. patent application Ser. No. 10/352,806
U.S. patent application Ser. No. 10/675,860
U.S. patent application Ser. No. 10/786,875
PCT Appln. PCT/US90/03907
Arts et al., *Nucleic Acids Res.*, 25:311-317, 1997.
Brady and Iscove, *Methods Enzymol.*, 225:611-623, 1993.
Busche et al., *J. Am. Pathol.*, 157:605-611, 2000.
Compton, *Nature*, 350:91-92, 1991.
Elbashir et al., *Methods*, 26:199-213, 2002.
Fink et al., *Am. J. Pathol.*, 157:1459-1466, 2000a.
Fink et al., *Laboratory Invest.*, 80:327-333, 2000b.
Gaynor et al., *Biotechniques*, 21: 286-291, 1996.
Klebe et al., *BioTechniques*, 21:1094-1100, 1996.
Liss, *Nucleic Acids Res.*, 30:89, 2002.
Li et al., *J Dent Res.;* 83(3):199-203, 2004.
Lockhart et al., *Nat. Biotechnol.*, 14:1675-1680, 1996.
Matsubara et al., *Hum. Immunol.*, 35:132-139, 1992.
Mesink et al., *Br. J. Haematol.*, 102:768-774, 1998.
Myers et al., *Biochemistry*, 30:7661-7666, 1991.
O'Leary, *Clin. Chem.*, 45:449-450, 1999.
Phillips and Eberwine, *Methods*, 10:283-288, 1996.
Retzel et al., *Biochemistry*, 19(3):513-518, 1980.
Silva et al., *Gut*, 50(4):530-4, 2002.
Su et al., *BioTechniques*, 22:1107-1113, 1997.
Tang et al., *J. Microbiol. Methods*, 39:121-126, 2000.
Tyagi and Kramer, *Nat. Biotechnol.*, 14:303-308, 1996.
Yan et al., *Anal. Biochem.*, 304:267-270, 2002.

What is claimed is:

1. A method comprising:
   a) mixing at least one biological unit containing RNA, a non-ionic detergent, and a buffer having a pH below pH 3.5 to prepare a low pH lysate; and
   b) mixing at least a portion of the low pH lysate directly with a composition comprising an enzyme that uses RNA as a substrate to form a reaction mixture;
   wherein the RNA is not isolated from the lysate prior to b), and
   wherein the lysate is not incubated with a protease prior to b); and
   wherein the method further comprises a step of detecting one or more protein(s) in the low pH lysate.

2. The method of claim 1, wherein the enzyme is in a buffer that adjusts the pH of the reaction mixture to a level suitable for enzyme function upon mixing.

3. The method of claim 1, wherein the buffer comprises an acid having a pKa of <3.

4. The method of claim 3, wherein the acid is arginine, glycine, or chloroacetic acid.

5. The method of claim 1, wherein the enzyme that uses RNA as a substrate comprises reverse transcriptase.

6. The method of claim 5, further comprising amplifying at least one cDNA product of the reverse transcription reaction.

7. The method of claim 5, further comprising determining the presence of and/or quantity of an RNA in the biological unit.

8. The method of claim 5, further comprising admixing an RNA control with the reaction mixture or the portion of the lysate prior to reverse transcription.

9. The method of claim 1, wherein the protein is detected in an antibody-based assay.

10. The method of claim 9, wherein the antibody-based assay comprises immunoblotting, ELISA, or immunoprecipitation.

* * * * *